US008690891B2

(12) United States Patent
Cowley et al.

(10) Patent No.: US 8,690,891 B2
(45) Date of Patent: Apr. 8, 2014

(54) STEERABLE SURGICAL SNARE

(75) Inventors: Collin George Cowley, Salt Lake City, UT (US); Creighton Ralph Petty, Salt Lake City, UT (US); Alexander David Snyder, St. George, UT (US); Andrew Steven Hansen, Eagle Mountain, UT (US); Tyler David Rees, Salt Lake City, UT (US); Kristofer Langheinrich, Louisville, KY (US)

(73) Assignee: University of Utah Research Foundation, Salt Lake City, UT (US)

( * ) Notice: Subject to any disclaimer, the term of this patent is extended or adjusted under 35 U.S.C. 154(b) by 473 days.

(21) Appl. No.: 12/830,060

(22) Filed: Jul. 2, 2010

(65) Prior Publication Data

US 2012/0004666 A1 Jan. 5, 2012

(51) Int. Cl.
*A61B 17/24* (2006.01)

(52) U.S. Cl.
USPC .................................................. 606/113

(58) Field of Classification Search
USPC ........... 600/104; 606/106, 110, 113, 114, 127
See application file for complete search history.

(56) References Cited

U.S. PATENT DOCUMENTS

| 4,886,067 | A | * | 12/1989 | Palermo | 600/434 |
|---|---|---|---|---|---|
| 5,417,684 | A | | 5/1995 | Jackson | |
| 5,906,621 | A | | 5/1999 | Secrest | |
| 6,007,546 | A | | 12/1999 | Snow | |
| 6,126,654 | A | * | 10/2000 | Giba et al. | 606/15 |
| 7,052,489 | B2 | * | 5/2006 | Griego et al. | 606/1 |
| 2003/0135222 | A1 | | 7/2003 | Baska | |
| 2005/0038424 | A1 | * | 2/2005 | Okada | 606/47 |
| 2005/0043743 | A1 | | 2/2005 | Dennis | |
| 2012/0004647 | A1 | | 1/2012 | Cowley | |

OTHER PUBLICATIONS

International Search Report Dated Jun. 29, 2011 Cited in Application No. PCT/US2011/042448.
U.S. Appl. No. 12/862,347, Mail Date Jan. 8, 2013, Office Action.
Written Opinion for PCT/US2011/042448 dated Jun. 29, 2011.
U.S. Appl. No. 12/862,347, Mail Date Jul. 15, 2013, Final Office Action.

* cited by examiner

*Primary Examiner* — Ashley Fishback
(74) *Attorney, Agent, or Firm* — Workman Nydegger

(57) ABSTRACT

Apparatus, assemblies, and methods for capturing objects within a body are disclosed. A surgical snare device includes a steerable deflection portion with a steerable distal tip. An interface is linked to the steerable deflection portion to selectively manipulate the distal tip. A snare loop disposed at the distal tip can have a length that remains substantially constant as the distal tip is deflected and the snare loop moves in concert with the distal tip. The distal tip may deflect up to at least one-hundred eighty degrees, while the snare loop moves a corresponding amount. A method includes extending a snare through a body lumen and to a location near an object. The snare may have a loop that changes positions while maintaining the same length. The loop may be placed around an object and then used to retrieve the object from the body lumen.

18 Claims, 10 Drawing Sheets

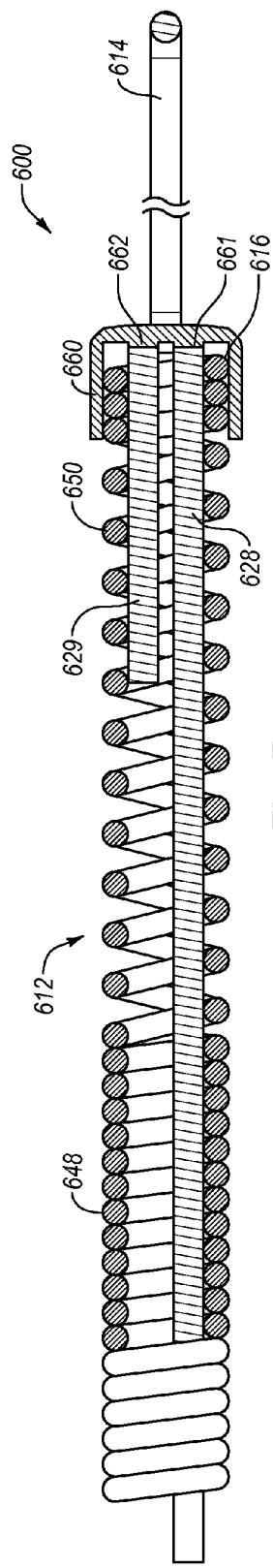

STEERABLE SURGICAL SNARE

FIELD OF THE INVENTION

The present disclosure relates generally to medical devices, and more particularly to surgical snaring instruments.

BACKGROUND OF THE INVENTION

Common surgical techniques make use of guide wires, catheters, stents, and other medical devices that may be placed within the body lumens of a patient. Such medical devices may occasionally break or fragment during installation, use, or retraction, thereby releasing all or a portion of the device into the patient's vascular system or other body lumens. In still other surgical procedures, sponges, gauze, or other medical materials may be inserted into an organ or vascular space, and left behind after surgery.

Medical devices or materials that fragment, break or are left behind in surgery are foreign to the body. In many circumstances, such foreign bodies may need to be removed for the patient's safety, health, or well-being. For instance, a foreign body may move through the bloodstream and potentially contribute to thrombosis, sepsis, arrhythmia, or a number of other complications. Accordingly, when an undesired foreign body is detected within a patient's organs or vasculature, it is typically desirable to remove the foreign body from the patient.

To remove the foreign body, a surgeon may resort to an open surgery technique; however, open surgery is often expensive, time consuming, and traumatic to the patient. Open surgery will often require longer healing times and result in greater risks of complications when compared to other, less invasive techniques. The risk of complication can increase if the patient has recently undergone another surgical procedure.

BRIEF SUMMARY

Example embodiments within the present disclosure relate to surgical devices and methods. Additional example embodiments of the present disclosure may relate to devices, assemblies, and methods for using a steerable snare to remove foreign bodies or other objects from a patient.

According to one exemplary embodiment, a surgical snare is described and includes a steerable deflection portion with a steerable distal tip. An interface may be linked to the deflection portion to provide for selective manipulation of the distal tip. A snare loop disposed at the distal tip may have a first length. As the distal tip is selectively deflected, the snare loop may also move between positions and the length of the snare loop at the distal tip may remain substantially constant.

In some embodiments, a steerable deflection portion may include a flexible elongate body. The body may be positioned between an interface and a distal tip. The distal tip may be configured to deflect substantially independently of the flexible body, and in response to selective manipulation of the interface.

In other embodiments, a distal tip may be a deflection tip that deflects by selectively bending between about zero degrees and about ninety degrees. In still other embodiments, the distal tip may deflect by selectively bending up to one-hundred eighty degrees or even up to three-hundred sixty degrees. A snare loop proximate the deflection tip may also selectively deflect a corresponding amount between about zero and about ninety or about one-hundred eighty degrees.

A surgical snare according to some embodiments includes a steerable deflection portion having a core wire. The core wire may be linked to an interface and can extend between the interface and a deflectable distal tip. Optionally, a deflection wire is located at the distal tip and configured to restrict compression of the steerable deflection portion and instead cause the steerable deflection portion to bend in response to a force applied to the core wire. The distal tip may deflect about the deflection wire such that the deflection wire is proximate an external curve of the distal tip in response to an interface applying the force to the core wire. To facilitate deflection, a steerable deflection portion may include a coiled shaft. The coiled shaft optionally has a tight coil and a loose coil. The loose coil may be proximate the distal tip of the surgical snare.

According to another example embodiment, a surgical snare is disclosed that includes a flexible body and a deflecting tip. The flexible body may define an axis and the deflecting tip may include a first and second state. A core wire may extend along the axis of the flexible body. A distal end of the core wire may be at least indirectly coupled to the deflecting tip. An interface linked to the proximal end of the core can selectively change between first and second positions. At a first position, the interface may cause the deflecting tip to be at the first state, and at the second position the interface may cause the deflecting tip to be at the second state. The second state may be at least ninety degrees offset from the first state. A snare loop coupled to the deflecting tip, and extending at least partially longitudinally relative to the flexible body, may be configured to move at least about ninety degrees as the deflecting tip transitions from the first state through the second state.

According to one embodiment, the core wire may be attached directly to a deflecting tip. Optionally, the deflecting tip may include a coiled shaft and a deflection wire. The deflection wire may be arranged to cause the coiled shaft to flex rather than compress as the interface moves between the first and second positions. The snare loop may also have a length that remains substantially constant as the snare loop moves in concert with the transition of the deflecting tip from the first state through the second state. The snare loop may be directly secured to the core wire, the flexible body, or the deflecting tip.

According to another embodiment, a method is disclosed for capturing an object through a body lumen. In the example method, a guidable snare may be extended through a body lumen to a location proximate an object. The guidable snare may include an elongate body, a deflectable tip coupled to the elongate body, and a snare loop portion linked to the deflectable tip. The snare loop may move between positions as the deflectable tip selectively deflects, and may also maintain substantially its same shape, length, width, or other dimension or configuration during such transitions. The object may be engaged with the snare loop portion by selectively deflecting the deflectable tip to at least partially cause the snare loop to transition from a first position to a second position. At the second position, the snare loop portion may extend around at least a portion of an object while maintaining its same shape, length, width, or other dimension or configuration.

According to another embodiment, a guidable snare may be extended through a catheter or other delivery tube and through a body lumen. The snare loop portion of the guidable snare may extend out a distal opening in the introduction or delivery tube. The guidable snare may also be retracted into the delivery tube. In retracting the guidable snare, the snare loop portion may have its shape changed as the snare loop portion is tightened around the object before the snare loop portion and/or object is retracted into the delivery tube.

According to some embodiments, first and second positions of the snare loop are offset by at least about ninety degrees. Selectively deflecting the deflectable tip may also include selectively bending the deflectable tip to cause the snare portion to transition from the first to the second position.

The guidable snare used in extracting an object may include a core wire with a distal end coupled to a deflectable tip. A user interface may be coupled to a proximal end of the core wire. Selectively deflecting the deflectable tip may cause the snare loop to transition from said first position to said second position and may include manipulating the user interface to cause the core wire to bend the deflectable tip by at least about ninety degrees. Bending of the deflectable tip and movement or other manipulation of the user interface may occur substantially in real-time. The snare loop may also be radiopaque, and extending the guidable snare through the body lumen may include monitoring a location and position of the snare loop using radiographic visualization.

In some embodiments, the steerable deflection portion is in a straight configuration when in a natural state. The natural state may be defined as when the steerable deflection portion is located outside of a catheter or the patient. For example, the natural state of a steerable deflection portion that is drawn or annealed during manufacturing would be the orientation in which the steerable deflection portion is left after manufacturing.

Additional features and advantages of example embodiments will be set forth in the description which follows, and in part will be obvious from the description, or may be learned by the practice of the invention. The features and advantages of the embodiments herein may be realized and obtained by means of the instruments and combinations particularly pointed out in the appended claims. These and other features of the present disclosure will become more fully apparent from the following description and appended claims, or may be learned by the practice of the invention as set forth hereinafter.

BRIEF DESCRIPTION OF THE DRAWINGS

Features and advantages of the embodiments of this disclosure will be apparent from the detailed description that follows, and which taken in conjunction with the accompanying drawings and attachments together illustrate and describe exemplary features of the disclosure herein. It is understood that these drawings merely depict exemplary embodiments and are not, therefore, to be considered limiting of its scope. Additionally, the drawings are generally drawn to scale for some example embodiments; however, it should be understood that the scale may be varied and the illustrated embodiments are not necessarily drawn to scale for all embodiments encompassed herein.

Furthermore, it will be readily appreciated that the components of the illustrative embodiments, as generally described and illustrated in the figures herein, could be arranged and designed in a wide variety of different configurations, and that components within some figures are interchangeable with, or may supplement, features and components illustrated in other figures. Nonetheless, various particular embodiments of this disclosure will be described and explained with additional specificity and detail through the use of the accompanying drawings, in which:

FIG. 7 illustrates a partial cross-sectional view of a spring having a distal cap;

FIGS. 8A and 8B illustrate example snare loop configurations according to some embodiments of the present disclosure.

DETAILED DESCRIPTION

Figure 1A:
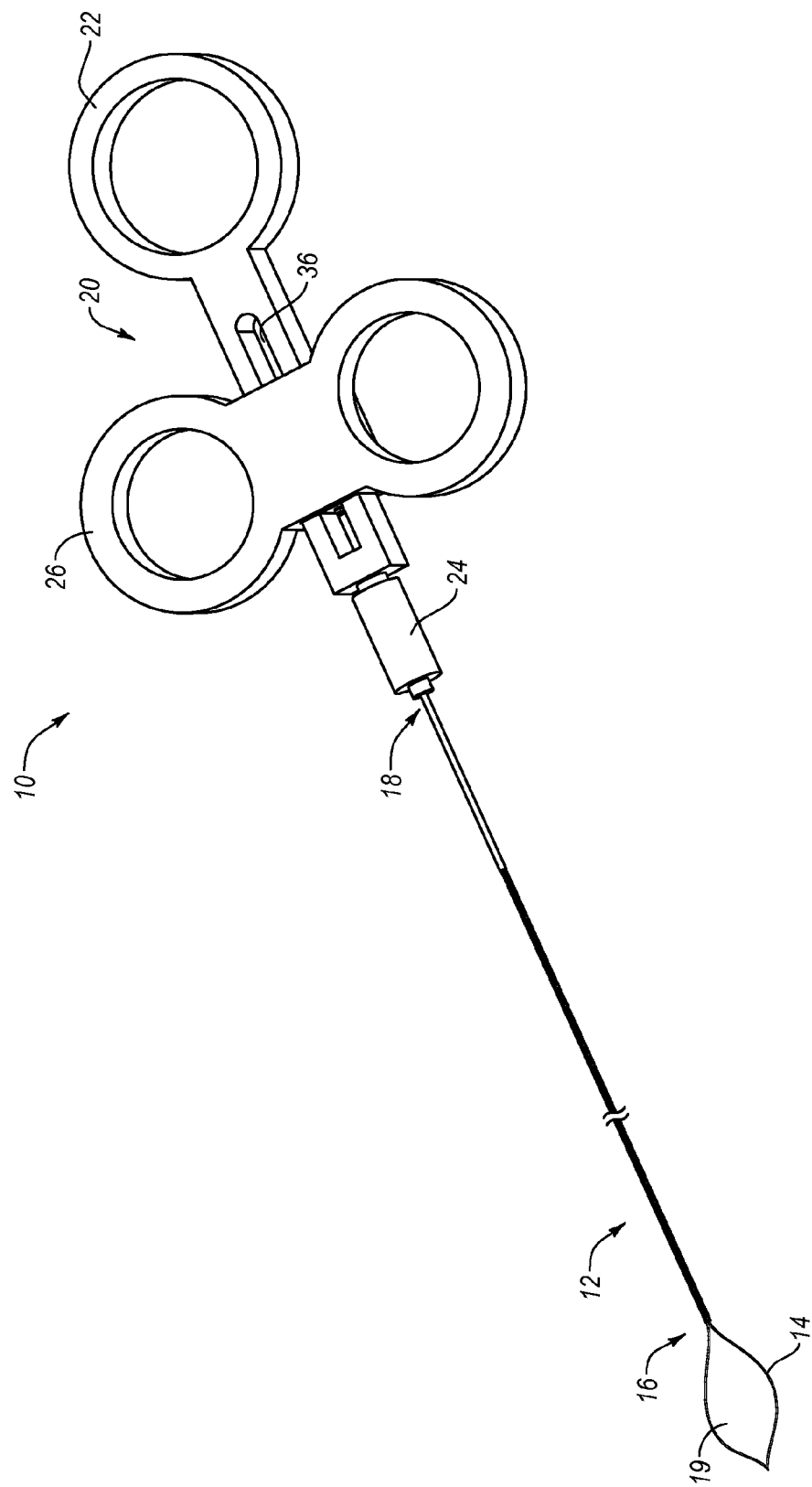
FIG. 1A illustrates an illustrative embodiment of a surgical snare according to one embodiment of the present disclosure.

The embodiments described herein generally extend to devices and methods for using a steerable surgical snare to remove objects from a body lumen. Some of the devices of the present disclosure are configured to remove objects from an organ, blood vessel, or other lumen of a patient through a minimally invasive surgical technique.

Challenges of traditional snare devices used in minimally invasive surgery may include the difficulty in capturing an object both within the size constraints of the vasculature or other body lumens of adult or pediatric patients and with the limited maneuverability that snare devices provide. Such challenges may be particularly apparent where fractures or other objects pose a grave threat to the patient's health, particularly where the orientation, size, shape, location, or other configuration of the object makes it difficult—if not impossible—to quickly capture and remove. By having a snare device that can be efficiently and predictably steered and re-oriented to snare objects of virtually any orientation, shape, or size within a body lumen, these challenges may be overcome, particularly in embodiments of a snare device that can move over a range of orientations in very small, if not infinitely small, increments. Such results, whether individually or collectively, can be achieved according to one embodiment of the present disclosure, by employing methods, systems, and/or devices as shown in the figures and/or described herein.

Reference will now be made to the drawings to describe various aspects of example embodiments of the disclosure. In the description, example surgical snares may be described with reference to snaring objects within vasculature, organs, or other body lumens. It should be appreciated that objects that can be captured and/or retrieved with a snare may include a variety of foreign or native objects. For instance, such objects may include foreign bodies introduced during a surgical procedure, or may include native bodies such as growths, polyps, tissue, vessels, or any other objects that are native to the patient and which are to be snared. It is further to be understood that the drawings are diagrammatic and schematic representations of example embodiments, and are not limiting of the present disclosure. Moreover, while various drawings are provided at a scale that is considered functional for some embodiments, the drawings are not necessarily drawn to scale for all contemplated embodiments. No inference should therefore be drawn from the drawings as to any required scale.

In the exemplary embodiments illustrated in the figures, like structures will be provided with similar reference designations. Specific language will be used herein to describe the exemplary embodiments, nevertheless it will be understood that no limitation of the scope of the disclosure is thereby intended. It is to be understood that the drawings are diagrammatic and schematic representations of various embodiments of this disclosure, and are not to be construed as limiting the scope of the disclosure, unless such shape, form, scale, function, or other feature is expressly described herein as essential. Alterations and further modifications of the inventive features illustrated herein, and additional applications of the principles illustrated herein, which would occur to one skilled in the relevant art and having possession of this disclosure, are to be considered within the scope of this disclosure. Furthermore, various well-known aspects of surgical procedures, catheterization, radiographic visualization, minimally invasive surgery, and the like are not described herein in particular detail in order to avoid obscuring aspects of the example embodiments.

Turning now to the drawings, FIG. 1A depicts an illustrative embodiment of a surgical snare 10 for capturing a foreign body, a native body, or some other object. The surgical snare 10 may, for instance, be used to engage, snare, encircle, control, or otherwise capture an object within the vascular system of a human or animal patient. In the illustrated embodiment, the surgical snare 10 may include a body 12. The body 12 may take a number of different forms. For instance, in the illustrated embodiment, the body 12 is elongate. In some embodiments, the body 12 may be elongate and tubular. Accordingly, the body 12 may also be referred to herein as an elongate tubular member 12, although a body 12 may have other shapes, sizes, constructions, or other configurations, or combinations of the foregoing. In some embodiments, the elongate tubular member 12 may be flexible. For instance, the elongate tubular member 12 may be sufficiently flexible so as to pass through a patient's vascular system in a minimally invasive procedure.

The surgical snare 10 may in some embodiments include a snare loop 14. In the illustrated embodiment, for instance, the snare loop 14 is disposed at a distal tip 16 of the elongate tubular member 12. More particularly, in this embodiment, the snare loop 14 may include a wire or other element that has a first end extending distally and/or longitudinally from the distal tip 16 of the elongate tubular member 12. The wire or other element may follow a generally elliptical path and loop back such that a second end of the wire or other element also connects at the distal tip 16. The snare loop 14 illustrated in FIG. 1A may define an opening 19 that can be used to receive and capture an object that is to be retrieved from a patient.

It should be appreciated that the snare loop 14 in FIG. 1A is merely exemplary. In other embodiments, the snare loop 14 may have other configurations, shapes, locations, or other features, or a combination of the foregoing. For instance, the snare loop 14 may follow a generally hexagonal, circular, rectangular, diamond-shaped, or other path, be cut from a solid material rather than formed from a wire, extend at least partially transverse relative to elongate tubular member 12, or have other configurations, or have any combination of such features. In some embodiments, and as described in greater detail hereafter, the distal tip 16 and/or the snare loop 14 may be steerable. For instance, even in embodiments in which the elongate tubular member 12 is flexible, the distal tip 16 may be selectively movable or deflectable relative to the elongate tubular member 12. In one embodiment, for instance, the distal tip 16 may be selectively deflected between zero and about one-hundred eighty degrees, such that the snare loop 14 also experiences a corresponding deflection. In such an embodiment, the snare loop 14 may optionally be deflected between zero and about one-hundred eighty degrees, and may effectively slide between such deflections such that any of virtually an infinite number of possible positions and deflected states of the snare loop 14 may be obtained.

To facilitate selective deflection of the distal tip 16 and the snare loop 14, a user interface 20 may be connected to the proximal end 18 of the elongate tubular member 12. More particularly, the user interface 20 may be used to provide an operator with a manual interface by which the operator can selectively deflect the distal tip 16 and/or the snare loop 14 of the surgical snare 10. In the embodiment illustrated in FIG. 1A, the user interface 20 may include a set of finger and thumb pieces connected to the proximal end 18 of the elongate tubular member 12. In particular, FIG. 1A illustrates a thumb piece 22 connected to the proximal end 18 of the elongate tubular member 12 through a cap 24. The illustrated cap 24 may be have an opening therein that receives at least a portion of the proximal end 18 of the elongate tubular member 12 to thereby connect the elongate tubular member 12 to the cap 24. The cap 24 may also connect to the thumb piece 22 and at least indirectly couple the elongate tubular member 12 to the thumb piece 22.

A finger piece 26 may also be connected to the thumb piece 22. In the illustrated embodiment, the finger piece 26 may be slideable or otherwise movable relative to the thumb piece 22. For instance, the finger piece 26 may have an opening into which the thumb piece 22 is received. The finger piece 26 may slide relative to the thumb piece 22 that is received within the opening. The relative movement between the finger piece 26 and the thumb piece 22 may be within or relative to a central groove 36, and/or may facilitate selective deflection or other movement of the distal tip 16 and/or the snare loop 14. As the finger piece 26 may slide or otherwise move relative to the thumb piece 22, the finger piece 26 may also be positioned at a virtually infinite number of discrete locations, which may also correspond to a virtually infinite number of discrete positions of the distal tip 16 and/or the snare loop 14. The finger piece 26 may therefore at least partially act as an actuation mechanism for selectively deflecting the snare loop 14 and/or the distal tip 16. For instance, as described in greater detail hereafter, an actuation mechanism may also include a wire or other filament or element (not shown) that is directly or indirectly coupled to the distal tip of 16 of the elongate tubular member 12. Such element may extend approximately an entire length of the elongate tubular member 12 and directly or indirectly attach to the finger piece 22.

To deflect the distal tip 16 and/or the snare loop 14, a surgeon or other operator of the surgical snare 10 may, for example, place index and middle fingers in the finger piece 26, and a thumb in the thumb piece 22. The operator may then draw the index and middle fingers towards the thumb, thereby also causing the finger piece 26 to move relative to the thumb piece 22. In moving the finger piece 26 in this manner, tension or another force may be placed on the actuation mechanism that connects to the distal tip 16, and the distal tip 16 may deflect in a desired manner. For instance, the distal tip 16 may bend from an unstressed state to a stressed state in which the distal tip 16 and/or the snare loop 14 are deflected between about zero and about one-hundred eighty degrees, although the snare loop 14 may deflect any other amount, including but not limited to up to one-hundred eighty degrees. The sliding motion of the finger piece 26 relative to the thumb piece 22 may, for example, correspond to a sweeping motion of the distal tip 16 and/or the snare loop 14 as the distal tip 16 bends over a virtually infinite range of angles between zero and one-hundred eighty degrees with respect to an original or unstressed orientation of the snare loop 14 and/or distal tip 16. For instance, the distal tip 16 and snare loop 14 may be oriented along the distal axis of the elongate tubular member 12. Upon manipulating the finger piece 26 and/or thumb piece 22, the distal tip 16 and snare loop 14 may bend up to one-hundred eighty degrees from the original or unstressed, longitudinal orientation.

In other embodiments, an original and/or unstressed orientation may be transverse relative to the longitudinal axis of the elongate tubular member 12. For instance, an original orientation may be at a right angle from the longitudinal axis such that a one-hundred eighty degree deflection in the distal tip 16 may result in the snare loop 14 also deflecting one-hundred eighty degrees. The resulting location of the snare loop 14 may also be at a right angle relative to the longitudinal axis. Accordingly, a deflection of one-hundred eighty degrees may result in a final or other orientation that is at any angle relative to a longitudinal axis of the elongate tubular member 12. Moreover, while deflection may be up to one-hundred eighty degrees, this is merely exemplary. In other embodiments, a maximum deflection is less than one-hundred eighty degrees (e.g., about ninety degrees) while in other embodiments, the maximum deflection is greater than one-hundred eighty degrees (e.g., about three-hundred sixty degrees), although any amount of desired deflection may be obtained.

With the distal tip 16 and/or snare loop 14 in a stressed or unstressed position, the snare loop 14 can be positioned around a foreign body or other object, or otherwise used to engage the object. The object can then be removed from the patient by drawing the thumb piece 22 away from the patient as the snare loop 14 engages the object. In some embodiments, such as those described hereafter, the snare loop 14 may also selectively contract and/or be tightened around the snared object. The snare loop 14 may be selectively contracted by, for example, drawing the snare loop 14 towards a delivery tube such as a catheter. In other embodiments, a wire or other filament or element may at least partially act as a second actuator that selectively pulls one end of the snare loop 14 to reduce the size of the snare loop 14. Other mechanisms may also be used to contract the snare loop 14. For instance, the snare loop 14 may be formed of a shape memory alloy and may contract, deform, or bias to a closed position when heat or an electrical current is supplied.

Figure 1B:
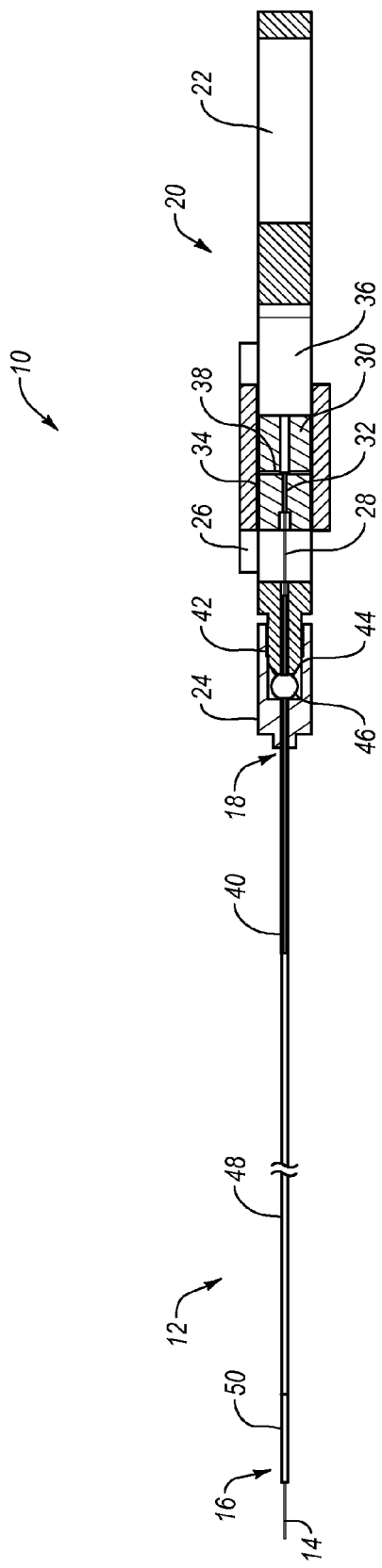
FIG. 1B illustrates a cross-sectional view of the surgical snare of FIG. 1A.

To further appreciate the manner in which the surgical snare 10 may be made and/or used, reference will now be made to FIG. 1B, which illustrates a cross-sectional view of the surgical snare 10 of FIG. 1A. In FIG. 1B, various internal components or aspects of the surgical snare 10 are illustrated to provide a greater understanding of the operation of surgical snare 10. It should be appreciated, however, that the surgical snare 10 of FIG. 1B is merely exemplary of one example surgical snare 10 according to the present disclosure and is therefore not intended to be limiting of the scope of the surgical snares or other apparatus or devices that may be learned by review of the disclosure herein.

In FIG. 1B, a wire 28 is illustrated as extending from the proximal end 18 of the elongate tubular member 12 and attaching to the user interface 20. In particular, in this embodiment, the wire 28 may be considered a core wire that extends longitudinally from the proximal end 18 towards an attachment member 30. In this embodiment, the attachment member 30 is disposed within the finger piece 26 of the user interface 20. For instance, the attachment member 30 may be a compression box or other box or member that receives and secures the wire 28.

More particularly, such a compression box or other member may have one or more openings 32 that are configured to receive the core wire 28. For instance, in FIG. 1B, the opening 32 extends along substantially the entire length of the compression box of the attachment member 30. The opening 32 may be sized so as to receive the core wire 28 therein. In some embodiments, the opening 32 may have a shape, size, or other configuration that is configured to cause an interference fit with the core wire 28 over at least a portion of the length of the opening 32. Moreover, the shape, size, or configuration of the opening 32 may be substantially constant along its length or may be variable. For instance, the opening 32 may have a constant size and shape along an entire longitudinal length thereof. In another embodiment, such as that illustrated in FIG. 1B, the opening 32 may vary along its longitudinal length. The distal end of the opening 32 may, for example, taper outward to provide a larger distal aperture through which the core wire 28 may be inserted into the attachment member 30. As the core wire 28 moves proximally within the attachment member 30, the size of the opening 32 may have a stepped or straight taper. With a stepped taper such as that illustrated in FIG. 1B, a portion of the elongate tubular member 12 may also extend into the attachment member 30. Optionally, the opening 32 may taper inward or outward from the interior of the attachment member 30 towards the proximal end of the attachment member 30.

As noted above, the core wire 28 may be secured to the attachment member 30 by using an interference fit. It should be appreciated, however, that other manners of connecting the core wire 28 to the attachment member 30 may also be used. For instance, in one embodiment, the core wire 28 is placed within the elongate tubular member 12 and the elongate tubular member is crimped at a proximal end thereof. Crimping the elongate tubular member 12 may secure the core wire 28 therein and allow the elongate tubular member 12 to then be secured within the attachment member 30. In some embodiments, crimping the elongate tubular member 12 may also generate greater real-time response. More particularly, as the user interface 20 is manipulated to actuate and selectively deflect the distal tip 16, a crimped elongate tubular member 12 may reduce lag time between pulling on the finger piece 26 and causing deflection at the distal tip 16. In still other embodiments, the core wire 28 may be secured to the attachment member 30 by using additional or other fastening techniques. In one example, an additional tubular member may be positioned around the proximal end of the core wire 28 and crimped in place. That tubular member may then be placed in the proximal end of the opening 32 of the attachment member. Such tubular member may also be crimped around the core wire 28 to lead to improved real-time response at the distal tip 16. In other embodiments, adhesives, mechanical fasteners, soldering, welding, or other fasteners, or combinations of the foregoing, may be used to secure the core wire 28 to the attachment member 30 or to the finger piece 26.

The attachment member 30 may indirectly couple the core wire 28 to the finger piece 26. For instance, the core wire 28 may be secured to the attachment member 30 and the attachment member 30 may be secured to the finger piece 26. In some embodiments, the attachment member 30 may be integrally formed as part of the finger piece 26. In other embodiments, the attachment member 30 may be formed separate from the finger piece 26. In an embodiment in which the attachment member 30 is not integrally formed with the finger piece 26, the attachment member 30 may be sized and shaped to be positioned within a central opening 34 of the finger piece 26, and/or to slide relative to the thumb piece 22 (e.g., within a central groove 36 of the thumb piece 22). The attachment member 30 may also be secured to the finger piece 26 in any suitable manner. For instance, in one embodiment, one or more set screws (not shown) may be used. A set screw may, for instance, extend through the finger piece 26 and into the attachment member 30. The attachment member 30 may also include a securement channel 38 configured to receive the one or more set screws and facilitate securement. As will be appreciated, any number of other securement devices, including adhesives, mechanical fasteners, interference fits, welding, soldering, or other devices, or any combination thereof, may also be used to attach attachment member 30 to finger piece 26.

As noted previously, in some embodiments, the exemplary core wire 28 may extend from the distal tip 16 of the elongate tubular member 12 to the user interface 20. As illustrated in FIG. 1B, the elongate tubular member 12 optionally includes a plurality of sections or portions through which the core wire 28 extends. In particular, the elongate tubular member 12 of FIG. 1B can includes three portions; however, more or fewer portions may also be included.

In FIG. 1B, a first portion 40 is disposed generally at the proximal end 18 of the elongate tubular member 12 and may be located at the connection between the elongate tubular member 12 and the user interface 20. The first portion 40 may include, for example, a tube that has a substantially solid construction. For instance, the first portion 40 may be a hypotube formed from extruded or molded stainless steel, NITINOL®. In other embodiments, however, the first portion 40 may be made from other materials, including other metals or alloys, as well as polymers, organic materials, composites, other materials, or any combination of the foregoing. The first portion 40 may form or define a cannula at the proximal end 18 of the elongate tubular member 12 and can, in some embodiments, be used to facilitate securement of the core wire 28 to the user interface 20. For instance, as described previously, the core wire 28 may extend through the first portion 40. The first portion 40 may be secured to the core wire 28 (e.g., by crimping), and the first portion 40 may be extended into the attachment member 30.

As further illustrated in FIG. 1B, the first portion 40 of the elongate tubular member 12 may be held in place by the cap 24 and the thumb piece 22. In the illustrated embodiment, the cap 24 includes a proximal channel 42. The thumb piece 22 may include a threaded connector 44 that can be threaded into the proximal channel 42. In some embodiments, the proximal channel 42 has a length greater than the length of the threaded connector 44 such that a void is created between the distal end of the threaded connector 44 and the distal end of the proximal channel 42. The first portion 40 of the elongate tubular member 12 may include, in some embodiments, a radius bulge 46 or other structure configured to fit within such a void. For instance, the radius bulge 46 may be sized to fit securely within the void such that the thumb piece 22 and the cap 24 hold the first portion 40 in place. The radius bulge 46 may also be eliminated in other embodiments. In one embodiment, for instance, an O-ring may be placed around the first portion 40 and between the thumb piece 22 and the cap 24 so as to facilitate securement of the elongate tubular member 12 to the user interface 20.

With the first portion 40 of the elongate tubular member 12 held in place, the second and third portions 48, 50 of the elongate tubular member 12 may also be held in place relative to the user interface 20. In some embodiments, the second portion 48 may be formed of the same or a similar material and/or have the same or a similar configuration relative to the first portion 40. In other embodiments, however, the first and second portions 48 may have different materials and/or configurations.

In one example embodiment, the first portion 40 may be a substantially solid tubular structure while the second portion 48 may have a coiled configuration. More particularly, the second portion 48 may be composed at least partially of a wire coiled to form a tubular structure. The coiled structure of such a wire may vary from embodiment to embodiment. In one example, a coiled second portion 48 may be tightly coiled. For instance, in a tight coil, each coil may be formed or otherwise located about directly proximate adjacent coils. More particularly, in some embodiments of a tight coil, the distance between the centers of adjacent coils may be about equal to the width of the coil wire. In other embodiments, however, the second portion 48 may have a different construction. For instance, the second portion 48 may have a loose coil construction or may be not be a coil. For example, the second portion 48 may be formed at least partially from a polymeric material (e.g., nylon or a polyamide) that is extruded or otherwise molded in a tubular configuration.

The second portion 48 may be connected to the first portion 40 in any suitable manner. For instance, the first and second portions 40, 48 of the elongate tubular member 12 may be formed from stainless steel, NITINOL®, some other biocompatible metal or alloy, or a combination thereof. First and second portions 40, 48 may then be soldered or welded together. In other embodiments, the second portion 48 may be threaded or otherwise secured within or around the first portion 40. In still other embodiments, epoxies, chemical fusing, or other connection mechanisms may be used.

As noted above, the elongate tubular member 12 may have multiple portions. In the embodiment in FIG. 1B, the elongate tubular member 12 has a third portion 50 that extends longitudinally from the second portion 48. In some embodiments, the third portion 50 may be formed of the same or a similar material and/or have the same or a similar configuration relative to the first or second portions 40, 48. In other embodiments, however, at least one of the first, second or third portions 40, 48, 50 may have different materials and/or configurations.

In one example embodiment, the second portion 48 may have a tightly coiled configuration. The third portion 50 may also have a coiled configuration, may have a solid tubular configuration, or may have some other configuration. In one optional embodiment, the third portion 50 includes a coiled configuration that is loosely coiled with respect to the second portion 48. For instance, the centers of the coils of the third portion 50 may be separated by a distance greater than the separation between the centers of coils in the second portion 48 and/or by a distance greater than the width of the sire forming the third portion 50. In one embodiment, for instance, adjacent coils of the second portion 48 may be about touching such that the center distance between coils in the second portion 48 may be approximately the coil wire width. In the third portion 50, however, the coils may be separated. For instance, the center distance between adjacent coils may be between 115% and 200% the width of the coil wire. It will be appreciated, however, that the center distance for a tight coil and/or loose coil may also be varied. For instance, a tight coil may vary between a center distance of 100% and 150% of the coil wire width. A loose coil may vary between a center distance of 105% and 300% of the coil wire width, although even greater coil distances may also be used for the loose coil.

An aspect of using coiled wires for second and third portions 48, 50 is that the coils are generally able to move relative to each other to provide flexibility to the elongate tubular member 12, while also giving the elongate tubular member 12 column strength to extend through a body lumen. As the coils may move relative to each other, the coils and/or portions of the coils can separate or draw closer to each other as necessary to bend or otherwise contour to the shape of a patient's vasculature, organs, or other internal structure. Moreover, because the coils provide column strength, the elongate tubular member 12 may be extendable through vasculature, organs, body lumens, and the like. In other embodiments, a portion of the surgical snare 10 may be extended even in the absence of a delivery tube such as a catheter or other similar device. For instance it may be difficult, invasive, or traumatic to extend a catheter fully through certain areas of the body, such as through the right ventricle of the heart and into the left or right pulmonary artery where an object is located. In such a case, the catheter may extend only partially towards the object. The column strength of the distal end 16 of the elongate tubular member 12 may then allow the elongate tubular member 12 to exit a distal opening of the catheter and be extended through these certain areas, such as through the right ventricle of the heart and into the left or right vascular artery. Thus, catheters may provide a manner of introducing the surgical snare 12 partially into a body lumen while the surgical snare 10 can then extend without a delivery tube or other device to the ultimate desired location. In other embodiments, the surgical snare 10 may be used with a catheter extending to a location proximate the retrievable object, or the surgical snare 10 may be used without any catheter or delivery device.

In view of the discussion herein, it should be appreciated that the construction and/or use of the surgical snare 10 of FIGS. 1A and 1B may thus be varied in a number of manners. For instance, the surgical snare 10 may have a size that varies. Such variation in size may be based at least in part on a number of factors, including the size of the body lumen in which it is intended to be used, the age or size of the patient, the location of the retrievable object, or other factors, or a combination of the foregoing. According to one embodiment, for instance, the elongate tubular member 12 has length of up to about 150 centimeters, although even greater lengths may be used. Of the length, the third portion 50 may have a loose coil of a length between about 10 mm to about 50 mm, although in some embodiments the length of the third portion 50 may be greater than 50 mm or less than 10 mm.

The elongate tubular member 12 may be configured to fit in a variety of different sizes of body lumens, catheters, or other devices or locations. In some embodiments, the elongate tubular member 12 is configured to fit in a catheter having an internal diameter of between four and eight French. For instance, the elongate tubular member 12 may have a diameter of approximately 0.85 mm although larger or smaller diameters are contemplated. In another example, the elongate tubular member 12 may have a diameter between about 0.5 mm and 1.5 mm. In other embodiments, the diameter of the elongate tubular member 12 varies across its length. For instance, the distal tip 16 of the third portion 50 may taper such that the size at the distal tip 16 is less than the size of the elongate tubular member 12 at the interface between the second and third portions 48, 50. In other embodiments, any or all of the first, second, and third portions 40, 48, 50 taper or otherwise have sizes that vary relative to each other or across their respective longitudinal lengths.

In embodiments in which the elongate tubular member 12 includes a coiled tubular structure, the wire used to corm the coil may itself have any of a number of different dimensions or other constructions. For instance, in some embodiments, the coil wire may have a diameter of approximately 0.15 mm although the coil wire may be larger or smaller. For instance, the coil wire may have a diameter between approximately 0.05 mm and 0.5 mm, although still larger or smaller wire could be used in other embodiments.

The example user interface 20 in FIGS. 1A and 1B may also be varied in a number of different manners. For example, the illustrated embodiment may allow the finger piece 26 to travel a distance along the central groove 36 that generally corresponds to a particular deflection at the distal tip 16. For instance, full travel of the finger piece 26 along the central groove 36 may correspond to a deflection of about ninety degrees, about one hundred eighty degrees, or about two hundred seventy degrees at the distal tip 16. In other embodiments, the amount of deflection possible by moving the finger piece 26 along the central groove 36 of the thumb piece 22 may vary by other amounts, including up to or exceeding three-hundred sixty degrees.

While the finger piece 26 may be movable relative to the thumb piece 22 in a manner that that travel of the finger piece 26 directly corresponds to the deflection at the distal tip 16 of the elongate tubular member 12, such an embodiment is also merely exemplary. In other embodiments, for instance, the finger piece 26 may be provided with some form of mechanical advantage that creates a ratio of displacement that is greater or less than approximately a 1:1 relationship between the finger piece 26 travel and the deflection at the distal tip 16. For example, gearing or some other mechanism may be used to make displacement of the finger piece 26 correspond to twice the displacement of the distal tip 16, half the displacement of the distal tip 16, or some other ratio.

Furthermore, the thumb and finger pieces 22, 26 of user interface 20 are merely example structures that may be used by an operator to control deflection at the distal tip 16. In other embodiments, other types of user interfaces may be used. In one embodiment, for instance, a handle may be used with a trigger mechanism coupled to the core wire 28. As the trigger is pulled, the core wire 28 may then also be pulled to cause deflection at the distal tip 16. In other embodiments, a torque device may be used. For instance, a dial may be connected to the core wire 28. When the dial is rotated, the core wire may be wrapped around a central shaft, thereby causing deflection at the distal tip 16. In still other embodiments, other user interfaces may also be used. For instance, in another embodiment, an exposed wire acts as a user interface. In another embodiment, multiple core wires may be used to control deflection and/or a filament controlling contraction of the snare loop 14 may be coupled to the user interface. In such an embodiment, multiple user interfaces or control mechanisms may be used. Accordingly, the user interface 20 could include multiple displacement, rotational or other members, or a combination thereof, to control the deflection tip 16 and/or the snare loop 14. Furthermore, while a core wire 28 is one manner of linking the user interface to the distal tip 16, any other suitable actuation mechanism may be used.

Various materials may also be used to produce the various components of the surgical snare 10. According to one embodiment, for instance, the user interface 20 may be made from polymeric materials. In other embodiments, however, metals, alloys, organic materials, composites, or other materials, or combinations of the foregoing may be utilized. The elongate tubular member 12 may also be made from any of numerous materials. In some embodiments, the elongate tubular member 12 is formed from a biocompatible material. For instance, the elongate tubular member 12 may be formed from a stainless steel alloy. In other embodiments, however, the elongate tubular member 12 may be formed from titanium, nickel, nickel-titanium alloys (e.g., NITINOL®), cobalt, chromium, platinum, stainless steel, or alloys thereof, or other materials, or combinations of the foregoing. Furthermore, any or all portions of the device 10 may be formed from materials that are cold worked, strain hardened, heat treated, or are otherwise formed to produce a desirable set of properties. In some embodiments, any or all portions of the surgical snare 10 may be coated with other materials, such as biocompatible materials. For instance, the elongate tubular member 12 may be coated with a biocompatible material. Such a coating may be applied to the entire tubular member 12. In embodiments with a coiled structure, the coating may alternatively or additionally be applied to the wire produced to form the coiled structure. An example biocompatible polymer that may be used to coat the elongate tubular member 12 is polytetrafluoroethylene (PTFE) although other polymers and/or other materials may also be used.

Figure 2:
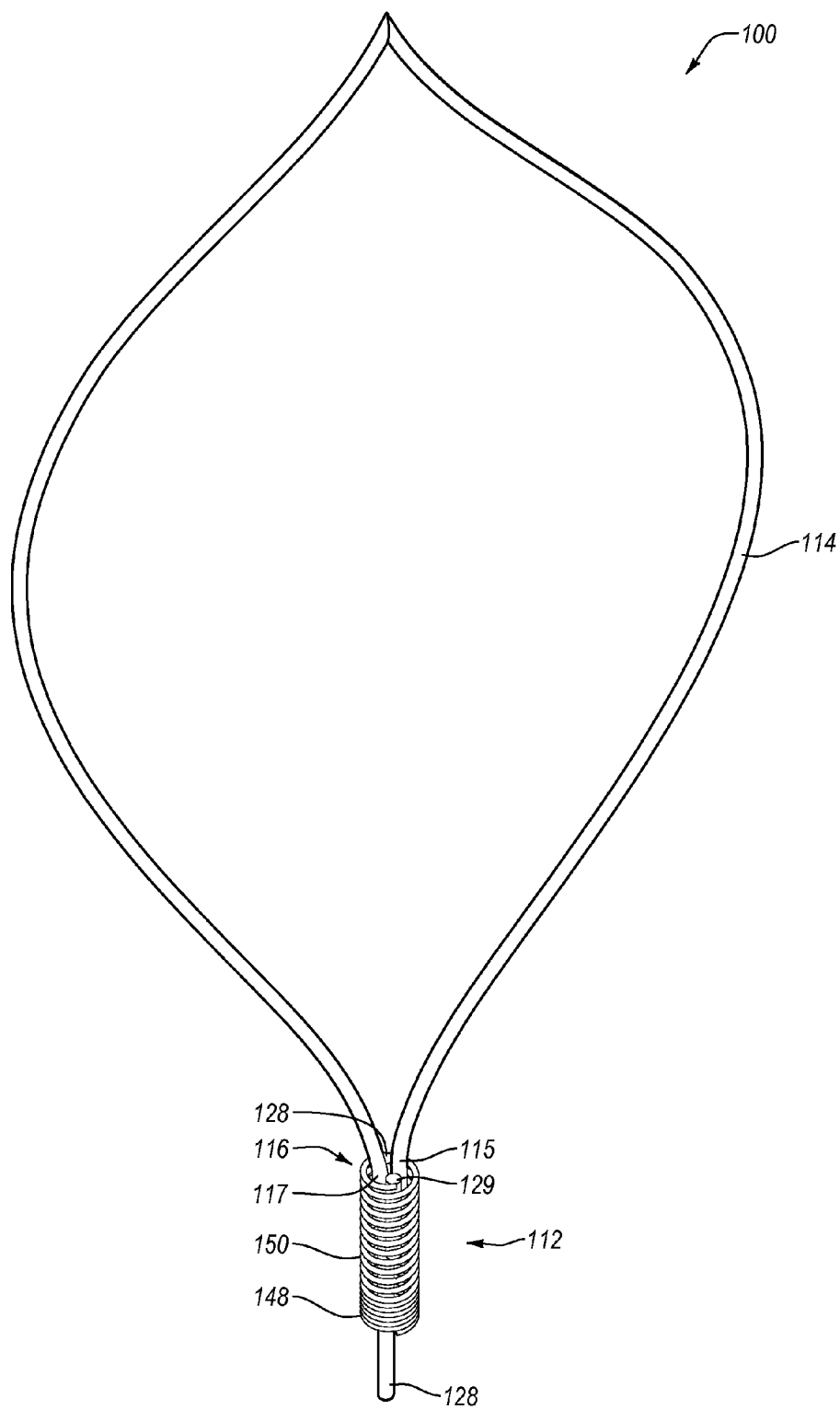
FIG. 2 illustrates a perspective view of a steerable distal tip of an example embodiment of a surgical snare.

Turning now to FIG. 2, a distal end of a surgical snare 100 is illustrated according to at least one embodiment of the present disclosure. In the illustrated embodiment, a snare loop 114 is connected to a distal tip 116 of a tubular member 112. The tubular member 112 may be similar to elongate tubular member 12 in FIGS. 1A and 1B. For instance, in this embodiment tubular member 112 includes at least a tight coil portion 148 and a loose coil portion 150. In the illustrated embodiment, the loose coil portion 150 is positioned adjacent the snare loop 114 and forms a part of the distal tip 116. In other embodiments other or additional types of coils or elements may be adjacent the snare loop 114 and/or form a part of the distal tip 116.

As shown in FIG. 2, multiple wires, filaments, or other elements may be positioned within the tubular member 112. In this embodiment, for instance, at least four wires may extend longitudinally within the tubular member 112. More particularly, FIG. 2 includes a core wire 128, a deflection wire 129, and two ends of snare wires 115, 117, although wires within the tubular member 112 may be referred to by any number of names or have any number of different purposes. In other embodiments, more and/or fewer wires may be used. For example, the deflection wire 29 may be removed. In other embodiments, the deflection wire 29 may be replaced by a coating, weld, other structure, or combinations of the foregoing.

The core wire 128 in FIG. 2 may be similar to the core wire 28 as described with reference to FIGS. 1A and 1B. For instance, the core wire 128 may extend substantially an entire length of the tubular member 112 and be connected to, or used as part of, a user interface that can control deflection of the distal tip 116 and/or the snare loop 114. In the illustrated embodiment, the core wire 128 may be connected to the distal tip 116 of the tubular member 112. For instance, the core wire 128 may be welded, soldered, mechanically connected, adhered, chemically fused, or otherwise secured, or a combination of the foregoing, to the distal tip 116 of the tubular member 112. In one embodiment, for instance, the core wire 128 may be laser welded to an interior surface of the tubular member 112, although such embodiment is merely exemplary and other connection methods may be employed, including such methods referenced herein.

As shown in FIG. 2, a deflection wire 129 may also be positioned about at the distal tip 116 of the tubular member 112. The exemplary deflection wire 129 may extend only partially along the longitudinal length of the tubular member 112, be shorter than the core wire 128, terminate prior to the core wire 128, or have other structures, or have any combination thereof. In this embodiment, for instance, the deflection wire 129 may extend partially along the loose coil portion 150 of the tubular member 112. The deflection wire 129 may also be connected to the tubular member 112, and such connection may be performed by using laser welding or another suitable method, or in other embodiments, may be coupled to the core wire 128 and/or the ends 115, 117 of the snare wire.

In one example embodiment, the deflection wire 129 is disposed at a location within the tubular member 112 that is generally opposed to the position of the core wire 128. More particularly, the deflection wire 129 is, in one embodiment, about one-hundred eighty degrees angularly offset from the core wire 128 about a central or longitudinal axis, although other offsets may be used. For instance, the deflection wire 129 may be adjacent the core wire 128 or offset at any angular interval between zero and one-hundred eighty degrees.

The deflection wire 129 may be used for any number of different purposes. In some embodiments, for instance, an operator of a surgical snare may selectively place tension in the core wire 128 using a user interface or some other mechanism. Where the core wire 128 is connected to the loose coil portion 150, the tension on the core wire 128 may tend to compress the loose coils together. It may, however, be desirable that the distal tip 116 of the surgical snare 100 bend rather than compress. The deflection wire 128 may also be directly or indirectly connected to the loose coils. As a result, when the core wire 128 undergoes tension in some embodiments, the deflection wire 129 may restrict compression of the loose coils. Consequently, the tension on the core wire 128 may result in bending or otherwise deflecting the loose coils rather than compressing the loose coils. As the loose coil portion 150 bends, the snare loop 114 may move with the distal tip 116. For instance, if tension on the core wire 128 causes the distal tip 116 to flex between zero and about ninety degrees, the snare loop 114 may also sweep along a path that moves from an initial position at zero degrees to a second position that is approximately ninety degrees offset from the initial position.

To facilitate corresponding movement between the snare loop 114 and the distal tip 116, the snare loop 114 may also be directly or indirectly connected to the distal tip 116 of the tubular member 112. In one embodiment, for instance, the snare loop 114 is formed from a wire that is bent to form a looped structure. More particularly, a first end 115 of the wire may extend distally and longitudinally out of the tubular member 112. The snare loop 114 may have a generally elliptical, gooseneck, hexagonal, rectangular, circular, diamond, or other shape. The wire may thus follow any such shape and a second end 117 of the snare loop wire may then connect back at the tubular member 112, such as is illustrated in FIG. 2.

In some embodiments, the first and second ends 115, 117 of the wire that forms snare loop 114 may also extend proximally and/or longitudinally into the interior of the tubular member 112. Such extension of the first and second ends 115, 117 of the snare loop wire may facilitate connection of the snare loop 114 to or proximate the distal tip 116 of the tubular member 112. In the illustrated embodiment, for instance, the first and second ends 115, 117 of the snare loop wire may be laser welded, microwelded, otherwise secured, or combinations thereof, to the interior of the loose coiled portion 150, the core wire 128, or the deflection wire 129, or to some other structure, or to any combination of the foregoing. For example, the first end 115 may be connected to the deflection wire 129 and the second end 117 may be connected to the core wire 128, as shown in Figure 2A.

As will be appreciated in view of the disclosure herein, the shapes, sizes, positions, numbers, structures, configurations, arrangements, and other features of the elements of the surgical snare 100 may be varied in a number of different manners. For example, while the illustrated embodiment depicts the tubular member 112, snare loop 114, core wire 128 and deflection wire 129 as having generally circular cross-sectional shapes, this is merely exemplary. In other embodiments, the tubular member 112, snare loop 114, core wire 128, and deflection wire 129, or any combination thereof, may have a different cross-sectional shape, or not be formed from a wire. For instance, the deflection wire 129 may be composed of a flat wire or from a bar. Such a flat wire or bar may have a generally rectangular cross-sectional shape and, in some embodiments, assists in predictably controlling the direction of the selective deflection of the tubular member 112. Any or all of the tubular member 112, the core wire 128, the deflection wire 129, or the snare loop 114 may also have other shapes, including elliptical, rectangular, hexagonal, diamond, octagonal, trapezoidal, or other shapes, or combinations of the foregoing.

The size of the various elements comprising the distal end 100 may also be varied. For instance, the tubular member 112 may have any number of different widths or diameters, and/or may be formed from a wire or other filament or element having different cross-sectional sizes or shapes. As a result, the interior and exterior widths of the tubular member 112 may vary. The sizes of the snare loop 114, the core wire 128, and the deflection wire 129 may thus vary based on the size of the lumen through the tubular member 112. For instance, in one embodiment, the interior diameter of the tubular member 112 may be about 0.55 mm. In such an embodiment, the core wire 128, deflection wire 129, and snare loop 114 may be sized such that the four illustrated wires form a diamond-shaped pattern within the tubular member 112, as illustrated in FIG. 2. For instance, each of the core wire 128, the deflection wire 129, as well as the first and second ends 115, 117 of the snare loop wire may have a width of approximately 0.15 mm to 0.18 mm. In other embodiments, the core wire 128, deflection wire 129, and first and second ends 115, 117 are arranged in a different pattern or have different sizes and/or the tubular member 112 has a different size. For instance, the tubular member 112 may have an internal width between about 0.35 mm and about 2.5 mm, although the tubular member 112 may also have smaller or larger widths in other embodiments. As the size of the interior of the tubular member 112 may be varied, the size of the core wire 128, deflection wire 129, and first and second ends 115, 117 of the snare loop wire may vary, although such variation may not be necessary. Additionally, or alternatively, the core wire 128, deflection wire 129, and first and second ends 115, 117 may form a circular, elliptical, irregular, or other pattern, or a combination thereof, within the tubular member 112.

Figure 3A:
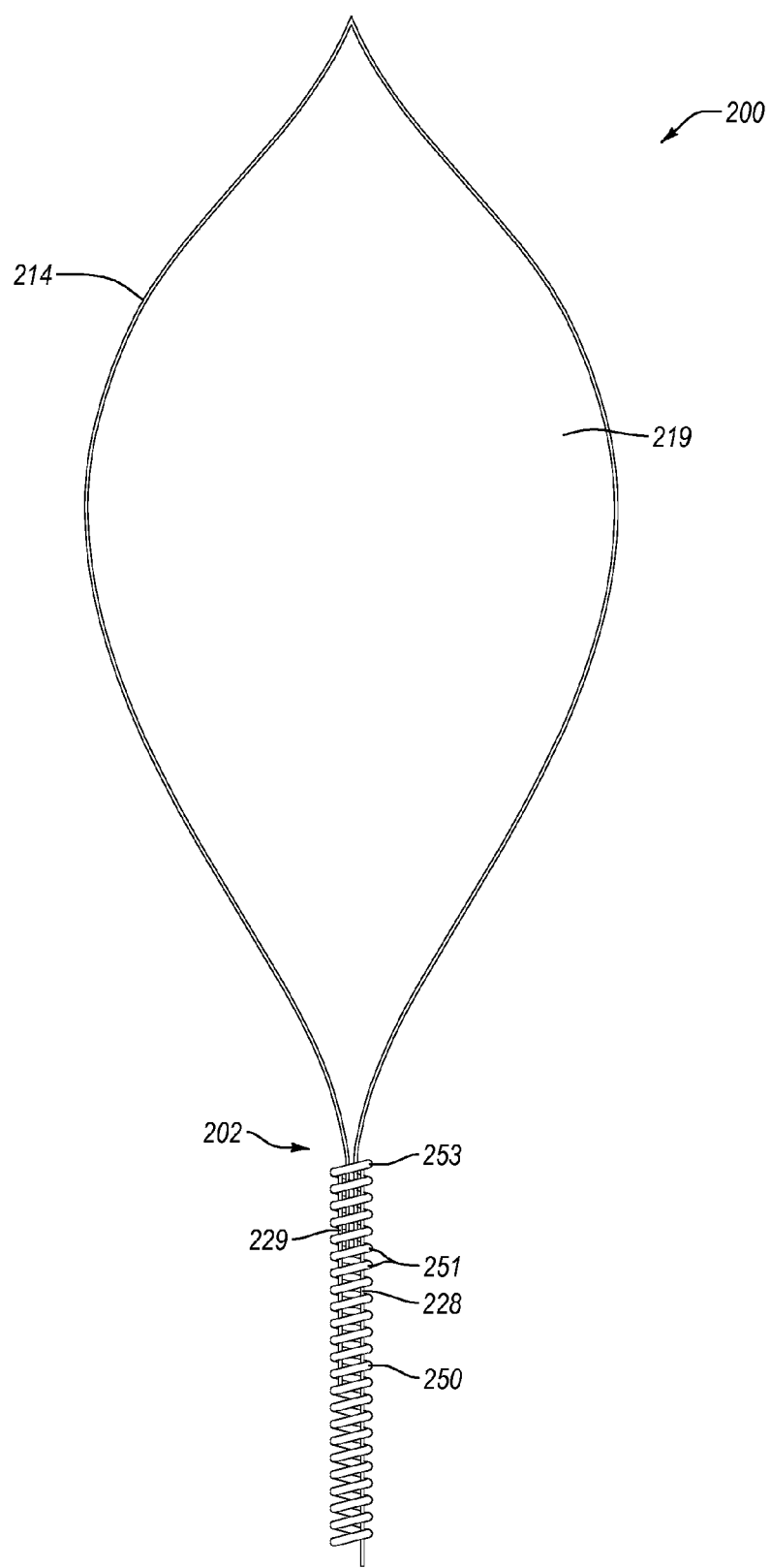
FIG. 3A illustrates a side view of a distal tip of an example surgical snare.
Figure 3B:
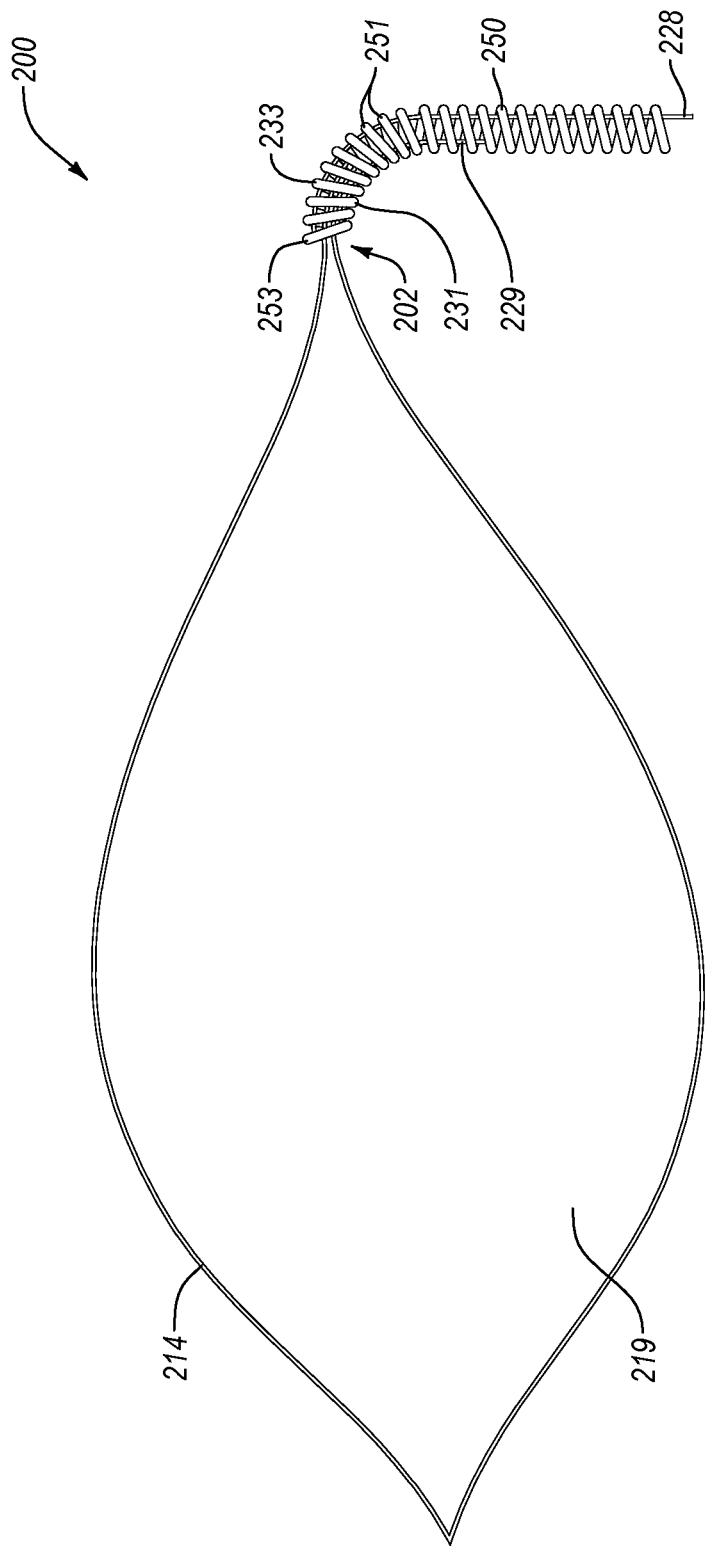
FIG. 3B illustrates a side view of the surgical snare of FIG. 3A, with the distal tip bent such that the snare is rotated about ninety degrees.
Figure 3C:
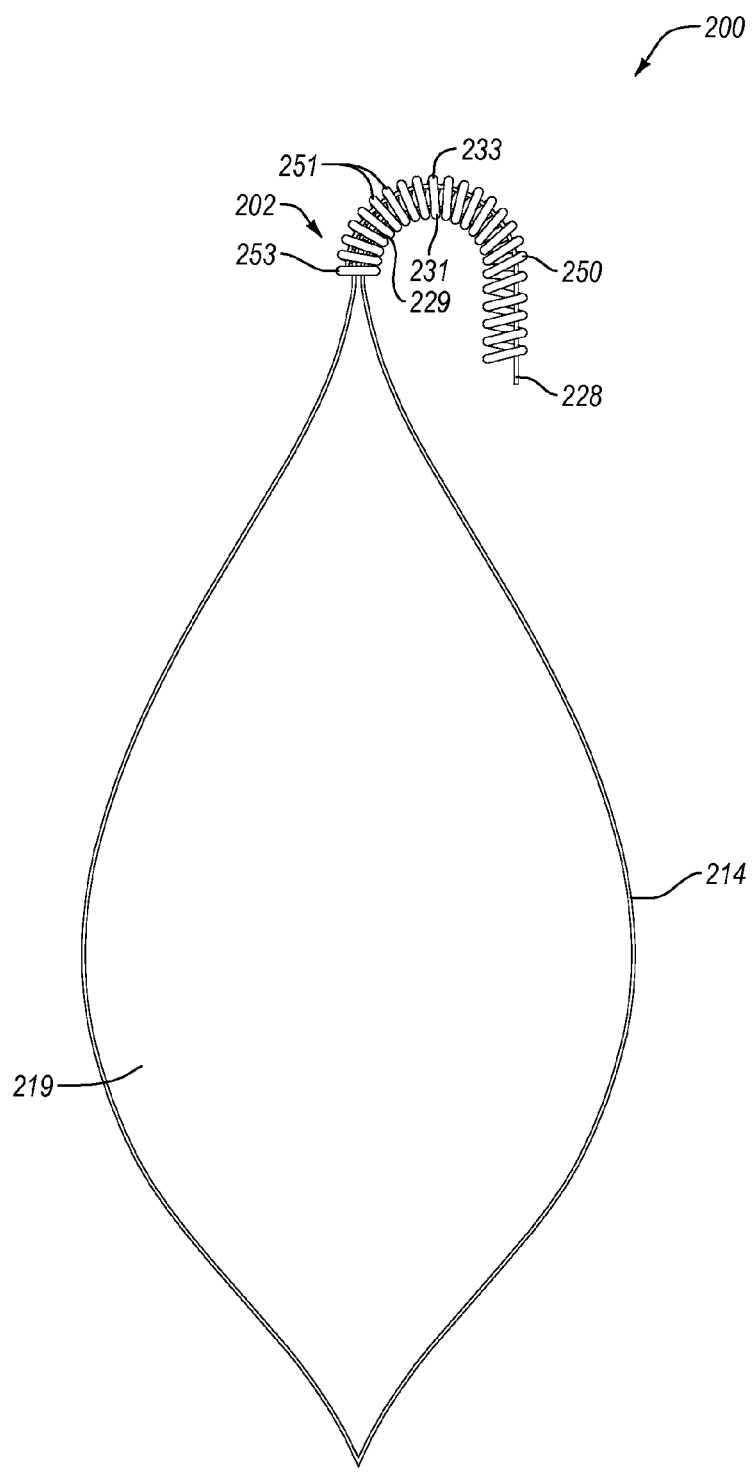
FIG. 3C illustrates a side view of the surgical snare of FIG. 3A, with the distal tip bent such that the snare is rotated about one hundred eighty degrees.

Turning now to FIGS. 3A-3C, an enlarged view of a distal end 202 of a surgical snare 200 is schematically illustrated in various stages of deflection. In FIG. 3A, for example, the surgical snare 200 is illustrated in a first state. The first state may, in some embodiments, correspond to an unstressed state. For instance, in an unstressed state, any tensile or compressive forces may be applied to the core wire 228 may be negligible, such that the core wire 228 has little or no tendency to cause the distal end 202 or a loose coil 250 to selectively bend or otherwise deflect. Instead, any deflection at the distal end 202 may be the result of the flexibility of the loose coil 250 and contact with an inner wall of a body lumen, either directly or indirectly (e.g., by following a delivery tube such as a catheter that contacts an inner wall of the body lumen). Accordingly, an unstressed or first state should not imply that the distal end 202 or the loose coil 250 must be straight as illustrated in FIG. 3A. Indeed, as noted in embodiments above, the loose coil 250 may have a plurality of coils 251 that provide flexibility to allow the distal end 202 to pass through a body lumen such as a blood vessel or organ. Such flexibility of the loose coil 250 may result from guiding the surgical snare 200 using a delivery tube such as catheter rather than from the selective deflection of the distal end 202 using the core wire 228 or some other actuation mechanism. In other embodiments, the first state may correspond to a natural state of a steerable deflection portion, i.e. core wire 228. As shown in FIG. 3A, the steerable deflection portion may be in a straight configuration when in the first, natural state. In further embodiments, the loose coil 250 may be curved by design, or otherwise curved or bent within a patient even in the absence of a catheter. Accordingly, no inference should be taken that a first or unstressed state should require the surgical snare 200, loose coil 250, or distal end 202 to have any particular shape or configuration. For instance, in an unstressed state, the loose coil 250 may even be bent up to ninety degrees; however, such bend may in one embodiment result from anatomical considerations rather than forces a user places on the distal end 202 by, for example, selectively pulling the core wire 228.

In the embodiment in FIG. 3A, the first state of the surgical snare 200 may include the snare loop 214 extending at least partially longitudinally relative to the tubular loose coil 250. In particular, in this embodiment, the snare loop 214 extends distally relative to a final, distal coil 253, and generally longitudinally with respect to the loose coil 250. In other embodiments, however, the snare loop 214 may extend in other directions. For instance, the snare loop 214 in the first state may be generally transverse relative to the loose coil 250. In one embodiment, for instance, the snare loop 214 may in a first state be positioned at any angle between about zero and about ninety degrees relative to a central axis of the loose coil 250. In other embodiments, the snare loop 214 may be positioned at an angle exceeding ninety degrees relative to the central axis of the loose coil 250. Moreover, the snare loop 214 may also extend longitudinally from the loose coil 250 as well as transverse relative to the loose coil 250. For instance, opposing wire ends of the snare loop 214 may extend longitudinally from the loose coil 250 and then be bent such that the loop portion extends transverse relative to the central axis of the loose coil 250.

As also shown in FIG. 3A, the snare loop 214 may have a generally open configuration in which the snare loop 214 defines a snare opening 219. The snare opening 219 may be sized, shaped, or otherwise configured to allow a foreign body or other object to be located at least partially therein and then retrieved using the surgical snare 200.

As discussed previously, a surgical snare according to some embodiments of the present disclosure may be selectively manipulated to change the position of the snare loop 214. For instance, according to at least one embodiment, the core wire 228 may be connected to the distal end 202 of the surgical snare 200. If the core wire 228 then has a force placed thereon, the distal end 202 may selectively deflect. Such selective deflection may be generally independent of other deflection along a longitudinal length of the tubular member 212.

FIG. 3B, for example, illustrates an example in which the surgical snare 200 has been manipulated to define a second state. In the second state, the distal end 202 of the surgical snare 200 has been deflected from the first state illustrated in FIG. 3A. More particularly, in FIG. 3B, the distal end 202 of surgical snare 200 has deflected about ninety degrees relative to the distal end 202 in the first state. Such deflection may at least partially result from a force being placed on the core wire 228. The force causing the deflection may be a tensile force in some embodiments, although compressive or other forces may also be used to cause a deflection at the distal end 202. In some embodiments, the deflection may additionally or alternatively result from a deflection member 229. In FIG. 3B, for instance, the deflection member 229 may be a wire that is also connected to the distal end 202 of the surgical snare 200. The deflection member 229 may extend at least partially along the length of the loose coil 250 and provide stiffness to allow the loose coil 250 to bend rather than compress when the core wire 228 is placed under tension. The second state may thus correspond to a stressed state. More particularly, in the example embodiment, the second state may be a stressed state for the surgical snare 200 in that a stress is placed on the core wire 228 to cause the distal end 202 to selectively deflect.

The loose coil 250 may facilitate deflection of the distal end 202 when the surgical snare 200 is in the stressed state. For example, in FIG. 3B, the distal end 202 may flex and define a curved path. In particular, the illustrated embodiment shows the plurality of coils 251 flex to define an interior curve 231 and an exterior curve 233. The interior curve 231 may have a length that is less than that of the exterior curve 233. For example, as tension is applied to the core wire 228, the tension may also be translated to the distal coil 253, causing the distal coil 253 to move. At the interior curve 231, the plurality of coils 251 may become compressed together. At the exterior curve 233, however, the loose coil 250 may expand and the plurality of coils 251 may further separate. Thus, as the interior curve 231 may be formed with a reduced arc length, the exterior curve 233 may be formed to have a greater arc length. In some embodiments, the interior curve 231 may generally correspond to the location of the deflection wire 229 and the exterior curve 233 may generally correspond to the location of the core wire 228, although such positioning is merely exemplary. For instance, in other embodiments, the deflection wire 229 may be generally proximate the interior curve 231.

With continued reference to FIG. 3B, it will be appreciated that upon deflecting the distal end 202 of the surgical snare 200, the snare loop 214 may also be re-positioned relative to the position of the snare loop 214 in the first state (FIG. 3A). For instance, when the distal end 202 flexes, bends, or otherwise deflects, the snare loop 214 may also move in a corresponding fashion. Where the distal end 202 moves approximately ninety degrees as shown in FIG. 3B, the snare loop 214 may also deflect by approximately ninety degrees. Thus, in some embodiments, the core wire 228 may be used to simultaneously deflect both the distal end 202 and the snare loop 214. Moreover, the snare loop 214 may be deflected without necessarily causing a change to the size or shape of the snare loop 214 or the snare opening 219. For example, as the snare loop 214 sweeps along a curved path from first to second states, the length, width, shape, or other configuration of the snare loop 214 may remain substantially constant. For instance, the deflection may not directly cause any change to the size or shape of the snare loop 214, although the walls of a body lumen 214 may directly or indirectly cause some deflection. During such deflection caused by external influences, the length and/or width of the snare loop 214 may remain substantially constant, even while the shape of the snare loop 214 may undergo minor changes. Furthermore, as the snare loop 214 may move between any position between that shown in FIGS. 3A and 3B, the snare loop 214 may effectively sweep along a curved path and be changeable in very small—if not infinitely small—angular increments.

The amount by which the distal end 202 and the snare loop 214 of the surgical snare 200 deflect may vary based on the amount of force applied to the core wire 228. For instance, the distal end 200 may be deflected any amount between zero degrees (e.g., FIG. 3A) and about ninety degrees (e.g., FIG. 3B). Even greater deflection may also be possible. For instance, in FIG. 3C, the surgical snare 200 is illustrated in a third state. In the illustrated third state, the distal end 202 has been deflected by about one-hundred eighty degrees. The third state may also correspond to a stressed state and may result from a force applied to the core wire 228. The force applied to the core wire 228 in the third state may be greater than the force applied to the core wire in the second state.

In the third state illustrated in FIG. 3C, the distal end 202 and the snare loop 214 of the surgical snare 200 have been deflected about one-hundred eighty degrees relative to the position of the distal end 202 in the first state illustrated in FIG. 3A. Such deflection may cause, for example the interior curve 231 and the exterior curve 233 to have a generally semi-circular shape. The arc length of the interior curve 231 may also be less than the arc length of the exterior curve 233 such that the coils 251 contract together along the interior curve 231 while being further separated along the exterior curve 233.

As shown in FIGS. 3A-3C, the snare loop 214 may thus be efficiently moved from an initial position to any number of positions and orientations by deflecting the distal end 202 of the surgical snare 200. For instance, by deflecting the distal end 202 by up to about one-hundred eighty degrees, the snare loop 214 can be oriented to engage a foreign body or other object around almost any curve, or which is in any location or position within a patient, particularly as the snare loop 214 may be swept along a curved path so as to selectively change between potentially a virtually infinite number of angular positions. The curved path may allow the snare loop 214 and distal end 202 to deflect or otherwise move both radially and longitudinally with respect to an otherwise stationary tubular member 212.

While FIGS. 3A-3C illustrate example surgical snares 200 that include a core wire 228 that may extend the length of the loose coil 250, a deflection wire 229, and snare loop wire ends 115, 117 that may extend only partially through the loose coil 250, it should be appreciated that such an illustration is merely exemplary. In other embodiments, for example, the number, length, position, or arrangement of wires or other elements may be varied. For instance, the deflection wire 229 may extend through a full length of the loose coil 250, extend at least partially into a tight coil portion of the tubular member 212, may be external to the loose coil 250, and/or may be excluded. The ends of the snare loop 214 may also extend through the loose coil 250, extend through or into a tight coil, be connected directly to an external portion of the tubular member 212 so as to not extend through any portion of the loose coil 250, have any other configuration, or a combination of the foregoing.

Figure 4:
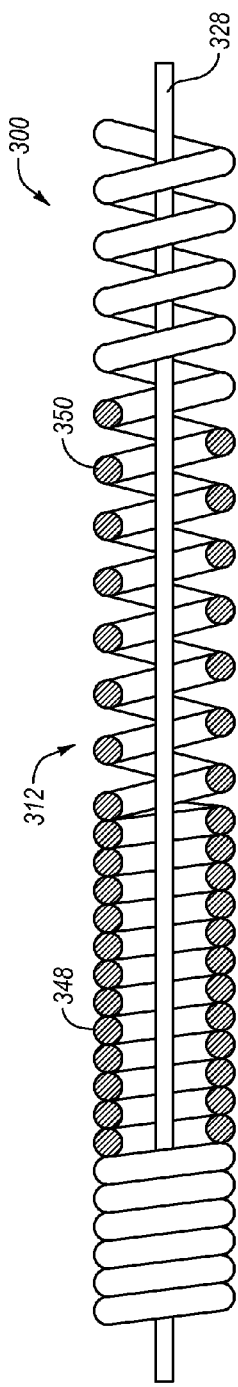
FIG. 4 illustrates a partial cross-sectional view of an embodiment of a spring having loose and tight coils, with a core wire therein.

FIG. 4, for instance, illustrates a partial cross-sectional view of a surgical snare 300 having a tubular member 312 with both a tight coil portion 348 and a loose coil portion 350. The surgical snare 300 of FIG. 4 may, but does not necessarily, correspond to the surgical snare 10 of FIGS. 1A and 1B. For example, the partial cross-sectional view in FIG. 4 may provide an enlarged view at an interface between exemplary second and third portions 48, 50 of the elongate tubular member 12 (FIG. 1A).

As shown in FIG. 4, a core wire 328 may extend at least partially through the tubular member 312. In the illustrated embodiment, the core wire 328 may extend fully through the illustrated tight coil 348 and loose coil 350. The core wire 328 may provide any number of features. For instance, as described herein, the core wire 328 may be linked to a distal tip of a surgical snare 300. An operator of such a surgical snare 300 may then push, pull, or otherwise control the core wire 328 to cause the distal tip of the surgical snare to bend or otherwise deflect. In deflecting the distal tip of the surgical snare, a corresponding snare loop may also be deflected to sweep along a path towards a desired position, orientation, or location. In other embodiments, the core wire 328 may be used for additional or other purposes. For instance, the core wire 328 may additionally or alternatively control the size of a snare loop. In another embodiment, the core wire 328 may deflect in multiple directions. For instance, if an electrical current is placed on the core wire 328, the core wire 328 may direct in one direction, whereas, pushing or pulling the core wire 328, placing a different electrical current on the core wire 328, or otherwise controlling the core wire 328 may cause the core wire 328 to deflect the tubular member 312 in a different manner.

Figure 5:
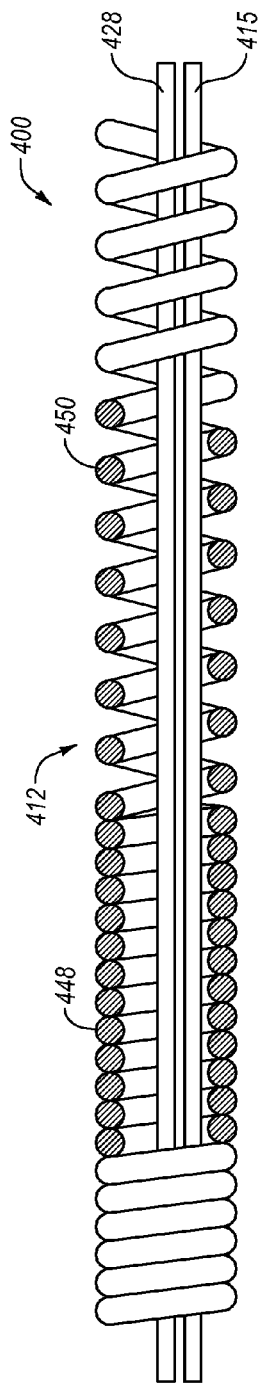
FIG. 5 illustrates a partial cross-sectional view of an embodiment of a spring having loose and tight coils, with a core wire and share wire therein.

In some embodiments, the core wire 328 may extend approximately the entire length of the tubular member 312. In other embodiments, however, the core wire 328 may extend only partially through the tubular member 312. For instance, an actuator may be positioned at an intermediate location along the tubular member 312 such that the core wire 328 extends only partially through the tubular member 312. In other embodiments there may be multiple wires, filaments, or other elements that extend fully or partially through a tubular member. For example, FIG. 5 illustrates an example portion of a surgical snare 400 in which multiple wires or other elements may extend through substantially the entire illustrated length of a tubular member 412. More particularly, FIG. 5 illustrates two wires or other filaments or elements extending through a tight coil 448 and loose coil 450 of a tubular member 412. The two elements may be used for any number of purposes or to accomplish any of a variety of different intents. According to one embodiment, the surgical snare 400 includes a first filament 428 that may act similar to a core wire as described herein. For example, the first filament 428 may run substantially an entire length of the tubular member 412 and be used to selectively deflect a distal tip and/or snare loop of the surgical snare 400. The first filament 428 may also run approximately a full length between a user interface and the distal tip of the surgical snare 400. Optionally, a second filament 415 may also be present. The second filament 415 can in some embodiments extend only partially through the tubular member 412. For instance, the second filament 415 may act as a deflection wire as described herein to provide stiffness or strength to facilitate deflection rather than compression of the tubular member 412.

In other embodiments, however, the second filament 415 may extend substantially an entire length of the tubular member 412, or substantially an entire length between a user interface and a distal tip of the surgical snare 400. For example, the second filament 415 may, in one embodiment, be connected to a first end of a snare loop. The second filament 415 may also not be directly secured to the tubular member 412. For instance, the second filament 415 may be configured to move within the tubular member 412. By way of example, an operator may pull on a proximal end of the second filament 415, either directly or by using a user interface. In embodiments in which the second filament 415 is connected to a snare loop, the force on the second filament 415 may pull the snare loop towards the tubular member 412 and change the shape or size of the snare loop, or pull all or a portion of the snare loop inside the tubular member 412. Such an action may be useful where, for example, the snare loop has been placed around a retrievable object and the operator desires to tighten the snare loop around such object. By pulling or otherwise manipulating the second filament 415, the snare loop can be tightened or otherwise changed as desired to secure the object.

The second filament 415 may also connect to other elements other than a snare a loop. For instance, in one embodiment, the second filament 415 may connect to the distal tip of the surgical snare 400 and provide a second mechanism for deflecting the distal tip and/or snare loop. For instance, the first filament 428 may be used to deflect the distal tip in one direction or manner, while the second filament 415 deflects the distal tip in a second direction or manner. Of course more or fewer filaments may also be included. For instance, three, four, or more filaments may be used to provide multiple actuators for selectively deflecting the distal tip of the surgical device 400 in a particular direction.

Figure 6:
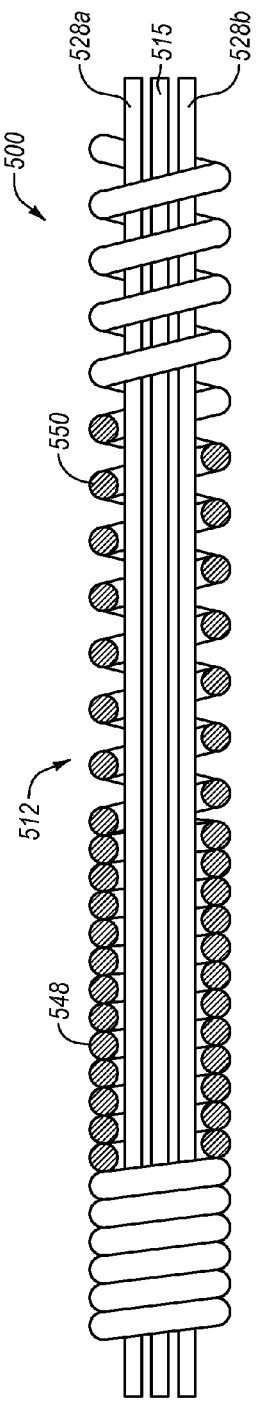
FIG. 6 illustrates a partial cross-sectional view of an embodiment of a spring having loose and tight coils, with two core wires and a snare wire.

FIG. 6 illustrates an additional embodiment in which three filaments may be disposed through a length of a tubular member 512 of a surgical snare 500. In this embodiment, the tubular member 512 of the surgical snare 500 optionally includes a tight coil 548 connected to a loose coil 550. Extending through both the tight and loose coils 548, 550 are three filaments 528a, 528b, 515. As discussed herein, such filaments 528a, 528b, 515 may have any number of configurations or uses. In one embodiment, the first filament 528a and second filament 528b each act similar to core wires described herein. For instance, each of the first and second filaments 528a, 528b may be independently and selectively manipulated to deflect a distal tip of the surgical snare 500 in a desired manner or direction. By way of illustration, a user may use a user interface at a proximal end of the surgical snare 500 to selectively tension the first filament 528a, which may cause the distal tip of the surgical snare 500 to flex or deflect in a particular direction or manner. Alternatively, the same or a different user interface or actuator may be used to tension the second filament 528b, which may cause the distal tip of the surgical snare 500 to flex or deflect in a different direction or manner. For instance, the second filament 528b may cause deflection in a direction that is about one hundred eighty degrees offset from the direction of deflection caused by the first filament 528a.

As further illustrated in FIG. 6, a third filament 515 may also extend at least partially through the tubular member 512 of the surgical snare 500. The third filament 515 may optionally act independent of the first and second filaments 528a, 528b. The third filament 515 may, for instance, be used to adjust the size of a snare loop of the surgical snare 500, cause the surgical snare 500 to bend or deflect in still an additional direction or manner, or cause some other reaction within the surgical snare 500, or any combination of the foregoing.

As discussed herein, regardless of the number of filaments that are positioned within all or a portion of the tubular member 512 of the surgical snare 500, such wires or other filaments may be secured to the tubular member 512 in any number of different manners. In one embodiment, for instance, wires may be laser welded at a distal tip of the surgical snare 500. In other embodiments, different methods for attachment such as those referenced herein may be used.

With reference now to FIG. 7, another surgical snare 600 is illustrated according to embodiments of the present disclosure, and which employs a cap 660 to attach one or more wires or other filaments to a tubular member 612. More particularly, FIG. 7 provides a partial cross-sectional view of a surgical snare 600 that includes a tight coil 648 proximate a loose coil 650. The loose coil 650 may be positioned at or proximate a distal end 616 of the tubular member 612 and adjacent a snare loop 614 at the distal end 616 of the surgical snare 600.

In the illustrated embodiment, a core wire 628 may extend through the interior of the tubular member 612 and terminate at approximately the distal end 616 of the tubular member. Such core wire 628 may be used to provide for the selective deflection of the distal end 616 of the tubular member 612, although other mechanisms for selectively deflecting the distal end 616 and/or the snare loop 614 may also be employed. Also at the distal end 616 in this embodiment is a cap 660 which may be threaded, adhered, welded, bonded, or otherwise coupled, or a combination of the foregoing, to the loose coil 650. For instance, the cap 660 may fit around an outer surface of one or more coils of the loose coil portion 650 although in other embodiments, the cap 660 may be positioned within or on the loose coil portion 650, or otherwise secured to the tubular member 612.

The cap 660 may be configured to receive or otherwise mate with the core wire 628 of the surgical snare 660. For instance, a receptor 661 may be formed on an interior surface of the cap 660, and sized and otherwise configured to mate with the core wire 628 and secure the core wire 628 to the cap 660. The cap 660 may then be secured to the distal end 616 of the tubular member 616 such that as a force is placed on the core wire 628, the force is translated to the cap 660, and from the cap 660 to the loose coil 650. For instance, if an operator places the core wire 628 under tension or compression, the core wire 628 may at least partially cause the loose coil 650 to bend or otherwise deflect a particular amount or direction.

In the illustrated embodiment, the cap 660 may also include a second receptor 662. The second receptor 662 may be used, for instance, to couple a second wire or filament to the distal end 616 of the surgical snare 616. In FIG. 7, for instance, a second filament may be a deflection wire 629 that can be used to facilitate flexure of the distal end 616 in response to a force applied on the core wire 628. In other embodiments, the second filament could include a second core wire, or another wire or other element.

While FIG. 7 illustrates cap 660 has having receptors 661, 662 specifically sized or otherwise configured to mate with wires 628, 629, it should be appreciated that this is merely exemplary. In other embodiments, the wires 628, 629 may be directly connected to the cap 660 by a welding, bonding, adhering, soldering, mechanically fastening, or other method, or a combination thereof, even in the absence of a specifically configured receptor. In other embodiments, the cap 660 may have an opening or groove therein to receive the wires 628, 629 so that the wires 628, 629 may be extended fully or partially through the cap 660 and secured in place relative to the cap 60 or the tubular member 612. For instance, the core wire 628 and/or the deflection wire 629 may pass through an opening in the cap 660 and then be knotted, soldered, welded, or otherwise secured at the exterior surface of the cap 660. Furthermore, an interface with the wires 628, 629, such as receptors 661, 662 may be excluded.

The cap 660 may thus facilitate connecting the core wire 628 and/or deflection wire 629 to the distal end 616 of the tubular member 612. Consequently, as the core wire 628 or other mechanism may be used to selectively deflect the distal end 616, the cap 660 can indirectly connect the core wire 628 to the loose coil 650 to cause the loose coil 650 to deflect in a selectively actuated manner. As the loose coil 650 deflects in the desired manner, the snare loop 614 may also experience a corresponding deflection or movement. To facilitate such corresponding deflection, the snare loop 614 can, in some embodiments, also be connected to the cap 660. The snare loop 614 may, for instance, be formed from a wire that has two ends that are coupled to the cap 660 in a manner similar to those described for the core wire 628 and/or deflection wire 629. By way of illustration, two ends of a wire forming the snare loop 614 may pass through one or more openings in the cap 660 and then be knotted, welded, soldered, bonded, otherwise secured, or a combination thereof, so as to secure the snare loop 614 to the interior surface of the cap 660. In other embodiments, receptors, or other attachment mechanisms may be used to secure the snare loop 614 to the exterior surface of the cap 660.

The snare loop 614 may have virtually any shape that may be used to retrieve an object from within a lumen of a patient. For instance, the snare loop may be circular, elliptical, hexagonal, or have other shapes or configurations. FIGS. 8A and 8B illustrate, for example, two snare loop configurations that are usable with the embodiments in this disclosure. FIG. 8A, for instance, illustrates a snare loop 714 having a generally elliptical, gooseneck configuration. In the illustrated embodiment, the elliptical snare loop 714 defines a substantially closed loop. In particular, snare loop 714 extends from a first proximal end 715 around a generally elliptical loop and terminates at a second proximal end 717. First and second proximal ends 715, 717 may be separated as illustrated in FIG. 8A, while still defining a substantially closed loop. In other embodiments, however, first and second proximal ends 715, 717 may touch to fully close the snare loop 714. In still other embodiments, the first and second proximal ends 715, 717 may cross or be connected together to close snare loop 714. For instance, FIG. 8B illustrates an alternative embodiment of a hexagonal snare loop 814 in which first and second proximal ends 815, 817 cross to fully close the snare loop 814.

As will be appreciated in view of the disclosure herein, snare loops according to the present disclosure may thus have various configurations. More particularly, a snare loop usable in connection with the present disclosure may have a variety of shapes, including elliptical, gooseneck, hexagonal, circular, rectangular, triangular, diamond-shaped, twisted, compound (e.g., multiple loops), among others, as well as have different sizes. For instance, a snare loop may be available in sizes ranging from approximately 5 mm in length to approximately 40 mm in length, although smaller or larger snare loops may also be used. Similarly, the widths of snare loops may also vary. For instance, a snare loop according to one embodiment of the present disclosure may range from approximately 2 mm in width to approximately 20 mm in width, although widths may also be smaller or larger. Thus, a snare loop according to the present disclosure may an elongate, regular, irregular, substantially closed, fully closed, or other configuration, or a combination of the foregoing.

With the continued evolution of minimally invasive procedures, minimally invasive procedures now also offer opportunities to capture and remove medical devices, fragments, or other objects that may be located within body lumens of patients. Such minimally invasive procedures may be less costly and time-consuming than traditional open surgery, with also a reduced risk of complication. In such a minimally invasive procedure, a retrieval device is typically used with fluoroscopy or some other visualization aid. An example retrieval device may include, for instance, a fixed snare that can be extended through a catheter and directed towards a foreign body in a body lumen of the patient. The distal snare may be positioned around an end of a foreign body and pulled against the catheter to tighten the snare around the foreign body. The retrieval device may then be pulled to drag the foreign body through the patient's body lumen until it can ultimately be retracted from the patient's body.

Such a snare instrument can thus provide an effective means for removing some foreign bodies in a minimally invasive manner to the patient. In some cases, however, the foreign body may be shaped, sized, or positioned in a manner that may make positioning of the snare difficult, if not impossible. In such cases, even a skilled surgeon may find it difficult and/or time consuming to place the snare around the fragment. It may take numerous attempts to change the orientation or location of the snare to effectively engage the foreign body. The difficulty in reorienting the snare can increase the time for the procedure and the trauma to the patient.

For example, even a skilled surgeon may have difficulty retrieving a foreign body with a retrieval device when that foreign body is located in a pulmonary artery. The left and right pulmonary arteries are accessible from the right ventricle of the heart; however, to reach the left and right pulmonary arteries with a retrieval device, the retrieval device must make a sharp bend that is approximately ninety degrees. To negotiate the turn, the retrieval device may have a turn radius that allows the retrieval device to bend about ninety degrees. Generally, the bend radius will cause the retrieval device to extend along an outer surface of the bend in the pulmonary artery. A foreign body to be retrieved may, however, be positioned along an interior surface of the bend in the pulmonary artery. Consequently, the surgeon may have difficulty orienting the retrieval device along the interior bend surface to capture and retrieve the foreign body. As the pulmonary artery is only inches away from the heart, objects within the pulmonary artery may also move around as the heart beats, thereby increasing the difficulty of snaring objects.

To facilitate retrieval of an object, some snares may be constructed such that a loop extends at a right angle from an elongate shaft of the retrieval device. Such a device may allow some objects to be more easily captured by the loop. However, by extending the loop at an angle relative to the retrieval device shaft, the width of the device is increased. The increased width may make insertion of such a retrieval device difficult or traumatic to the patient.

Figure 9A:
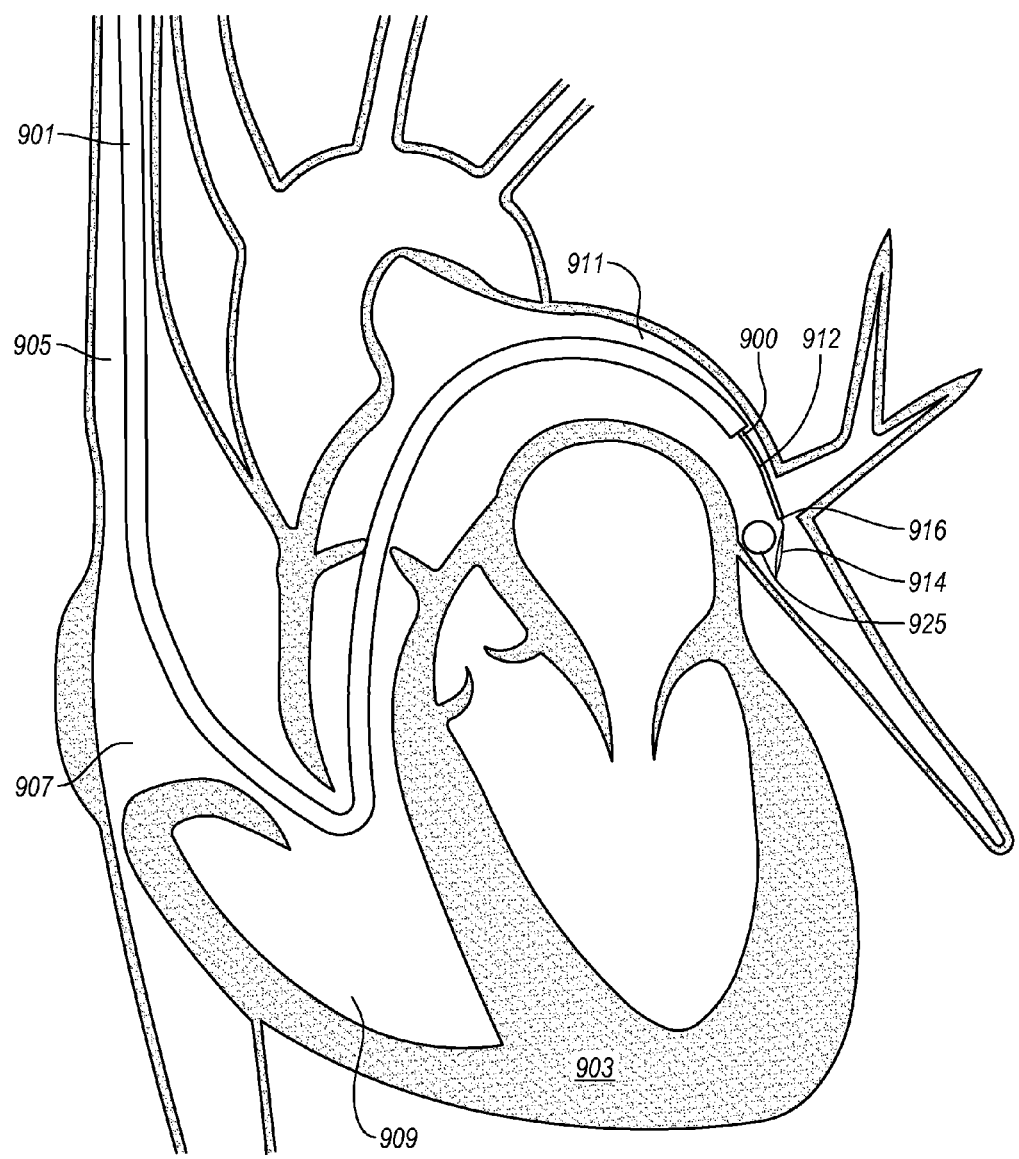
FIGS. 9A and 9B illustrate an example method in which an object inside a pulmonary artery may be retracted using a steerable surgical snare of the present disclosure.
Figure 9B:
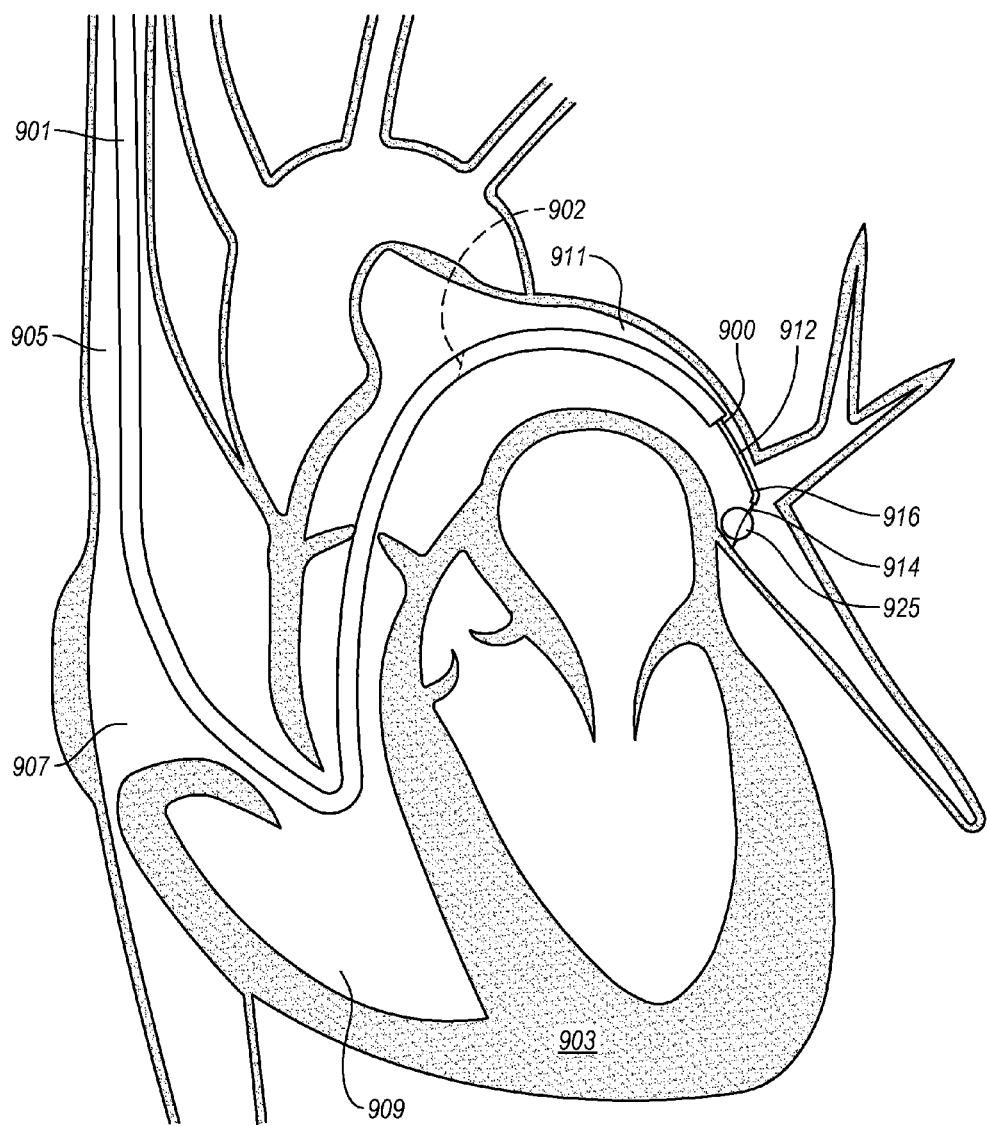

Turning now to FIGS. 9A and 9B, one example retrieval method according to the present disclosure is illustrated. In the illustrated embodiment, pulmonary artery catheterization may be used to remove an object within the pulmonary artery of a patient. In the illustrated embodiment, a delivery tube such as a catheter 901 may be introduced through a large blood vessel of the body (e.g., an internal jugular, subclavian or femoral vein), although any other vessel that may be used to grant the catheter 901 access to the heart 903 may also be used. From the entry site in such vessel, the catheter 901 may be directed through the patient's body through the heart 903. More particularly, as shown in FIGS. 9A and 9B, the catheter 901 may be directed through the superior vena cava 905 and into the right atrium 907. From the right atrium 907, the catheter 901 may be directed into the right ventricle 909, and ultimately into the pulmonary artery 911.

A visualization technique may be used to assist a surgeon in directing the catheter 901 into the position illustrated in FIG. 9A. For example, a surgeon may use a radiographic visualization technique such as fluoroscopy to obtain real-time images of the location of the catheter 901, although other suitable visualization techniques may also be used. The catheter 901 may be formed or modified in a manner that causes it to be visible for any particular visualization technique. In fluoroscopy, for example, the catheter 901 may be made radiopaque to prevent or restrict fluoroscopic radiation from passing through the catheter 901, thereby making the catheter 901 visible on a fluoroscopic display. The catheter 901 may, for example, have a radiopaque dye or contrast media coated thereon or injected therein. The catheter 901 may also be formed with radiopaque fillers such as barium, bismuth, and tungsten. The catheter 901 may additionally, or alternatively, have radiopaque marker bands applied thereto. For instance, bands of platinum, gold, iridium, tantalum, or other radiopaque materials, or combinations of the foregoing, may be placed on or in the catheter 901 to make the catheter 901 visible during radiographic visualization.

With the catheter 901 in place, a surgical snare 900 may be located within the patient to capture an object 925 within the patient. In the illustrated embodiment, the surgical snare 900 is placed through the catheter 901 and extended out the distal end of the catheter 901, further into the pulmonary artery 911. As shown in FIG. 9A, the pulmonary artery 911 may have a sharp bend that approximates ninety degrees. While the catheter 901 and the surgical snare 900 may be flexible, the catheter 901 and/or surgical snare 900 may be difficult to position directly against an object 925. In the illustrated embodiment, for instance, the object 925 is positioned on an interior side of a curve within the pulmonary artery 911. As the catheter 901 is extended through the pulmonary artery 911, the catheter 901 tends to extend around the outer profile of the curve. Such positioning of the catheter 901 thus makes it difficult for the surgical snare 900, as it exits the distal opening of the catheter 901, to directly engage the object 925.

As will be appreciated in view of the disclosure herein, a surgical snare 900 according to the present disclosure may effectively engage and optionally retrieve an object 925 even in locations that are difficult to access, and with little or no difficulty in passing the surgical snare 900 through the catheter or in a manner that causes unnecessary trauma to the patient. In some embodiments, the surgical snare 900 may be selectively steered to engage the object 925 and/or otherwise configured to engage the object 925. In FIG. 9A, for instance, the snare loop 914 is selectively steerable and also extends at an angle from the shaft 912 of the snare 900. In this particular example, the snare loop 914 is at approximately a thirty degree angle relative to the shaft 912. At about thirty degrees, the snare loop 914 may extend through the catheter 901 with minimal deformation. However, as the snare loop 914 extends from the catheter 901, the angled position may allow engagement with the object 925 to occur even prior to selectively steering the snare 901. It should be appreciated that the example angle of the share loop 914 at about thirty degrees is merely exemplary. For instance, in some embodiments, the snare loop 914 may be positioned at an angle between zero and one-hundred eighty degrees relative to the shaft 912.

In some cases, the object 925 in FIG. 9A may be difficult to access even with the snare loop 914 oriented at an angle relative to the shaft 912. Accordingly, the distal end 916 and the snare loop 900 of the surgical snare 900 may be steerable to reach the object 925. By way of illustration, the distal end 916 of the surgical snare 900 may be selectively steerable. Accordingly, the distal end 916 may be steered or guided independent of the overall flexibility of the shaft 912, so as to deflect the snare loop 914 into a position that may engage the object 925.

As shown in FIG. 9B, for instance, the surgical snare 900 of FIG. 9A has been selectively guided in a manner that allows the snare loop 914 to engage the object 925. More particularly, the distal end 916 of the shaft 912 in FIG. 9B has been deflected along a curve and between about zero and about ninety degrees. The snare loop 914 has also rotated and swept along a curved path that corresponds to about ninety degrees of rotation relative to the position of the share loop 914 illustrated in FIG. 9A. In the position illustrated in FIG. 9B, the snare loop 914 can engage and retrieve the object 925 that is against an interior side of the curve within the pulmonary artery 911, even without redirecting the shaft 912 against the interior side of the curve. In some embodiments, the snare loop 914 may be deflected and the surgical snare 900 may be then moved longitudinally within the catheter 901 to engage the snare loop 914 against the object 925.

Further, because the snare loop 914 can be swept along a curved path and positioned at any of a virtually infinite number of positions along the path, the surgical snare 900 can be passed through the catheter 901 with little difficulty, and without causing unnecessary trauma to the patient. For instance, a snare loop 914 that is fixed at a ninety degree angle relative to the longitudinal axis of the surgical snare may pass through a catheter, but may be required to deform to fit within the catheter. The interior surface of the catheter may cause the deformation and increase the resistance to passing the snare through the catheter. Additionally, or alternatively, a catheter of a larger size may be used to reduce the difficulty in passing the snare through the catheter; however, the larger catheter size can increase the trauma to the patient. In the illustrated embodiment, however, the surgical snare loop 914 may optionally be oriented in a generally longitudinal direction relative to the shaft 912 of the surgical snare 900. Such orientation may decrease the deformation of the snare loop 914 within the catheter, thereby allowing the surgical snare 900 to be more easily extended through a catheter, or even through a body lumen without a catheter, as well as through a catheter of a reduced size. Further, as the snare loop 914 can be selectively swept along a path to any of a virtually infinite number of positions, the snare loop 914 may effectively snare an object as it is moved to a desired position once outside the catheter 901 or after being deflected and further moved. As the snare loop 914 is deflected once outside the catheter 901, the size, length, width, shape, or other dimensions of the snare loop 914 may remain relatively constant and enable effective snaring of the object 925.

Once the snare loop 914 has been positioned such that it can be engaged around the object 925, the surgeon or other operator may move the surgical snare 900 to engage the object 925. To do so, the surgeon may also use a visualization or other technique. The surgeon may, for example, use the same visualization technique used to position the catheter 901. Accordingly, and by way of example only, the surgical snare 900 may also be radiopaque for a surgeon using a radiographic visualization technique such as fluoroscopy. To provide the surgical snare 900 with radiopaque properties, the materials used in the surgical snare 900 may be radiopaque. For instance, the shaft 912 and/or snare loop 914 may be formed or coated with a radiopaque material. The shaft 912 and/or snare loop 912 may, for instance, be formed from or coated with, a stainless steel alloy, titanium, nickel, nickel-titanium alloy, cobalt, chromium, gold, platinum, or other material, or any combination of the foregoing.

To further facilitate positioning of the surgical snare 900 relative to the object 925, the catheter 901 may be positioned proximate the object 925 as generally illustrated in FIGS. 9A and 9B. In this manner, the surgical snare 900 may be extended out the distal end of the catheter 901 and be positioned adjacent the object 925. In other embodiments, however, the surgical snare 900 may be extended greater distances, and the catheter 901 may not be capable of being positioned proximate the object 925 due to, for example, size constraints, material choices, and the like. For instance, in another embodiment, the catheter 901 may extend only partially into the superior vena cava 905, the heart 903, or the pulmonary artery 911 and the shaft 912 of the surgical snare may then extend a significant distance out of the catheter 901 before reaching the object 925. For instance, the distal end of the catheter 901 may generally correspond to the location of distal end 902 illustrated in phantom lines in FIG. 9B. The snare 900 may have sufficient column strength to extend distally from the distal end 902 around the bend in the pulmonary artery 911 and ultimately to a destination proximate the object 925. In other embodiments, the surgical snare 900 may have sufficient column strength to be used without any type of delivery tube.

Regardless of the manner of locating the surgical snare 900 and engaging the object 925 for retrieval, the surgical snare 900 may then be manipulated to hold the object 925 as the surgical snare 900 is retreated through the heart 903 and out of the patient. In one embodiment and as discussed herein, the snare loop 914 of the surgical snare 900 may be selectively retractable. In such an embodiment, an operator may pull or otherwise manipulate a wire or other element that causes the size of the snare loop 914 to be reduced, and to draw tightly around the object 925. The surgical snare 900 may then be extracted from the patient along with the object 925.

In another embodiment, a user can use the catheter 901 to selectively reduce the size and/or shape of the snare loop 914 for retrieval of the object 925. For instance, the catheter 901 may be placed proximate the object 925 such that as the surgical snare 900 is drawn in a proximal direction, the snare loop 914 begins to enter the distal end of the catheter 901. As the snare loop 914 is drawn into the catheter 901, the proximal ends of the snare loop 914 become enclosed in the catheter 901, and by continuing to draw the snare loop 914 into the catheter 901, the snare loop 914 may deform and collapse, thereby causing the snare loop 914 to draw tightly around the object 925. Thus, embodiments of the present disclosure contemplate selectively collapsing the snare loop 914 by using the catheter 901 or independent of the catheter 901.

Once the snare loop 914 is sufficiently tight around the object 925, the surgical snare 900 may be fully retreated. In embodiments in which a catheter 901 is used, the snare 900 may be drawn fully into the catheter 901 and extracted from the patient. To allow the object 925 and snare loop 914 to be more easily drawn into the catheter 901, the distal end of the catheter 901 may be angled. For instance, the distal end of the catheter 901 may be cut or formed at an angle between about thirty and about sixty degrees, although larger or smaller angles may be used. In other embodiments, the catheter 901 may have a blunt distal end.

While the illustrated embodiment illustrates a surgical snare 900 in which the snare loop 914 extends longitudinally from the shaft 912, it should be appreciated in view of the disclosure herein that this is merely exemplary. In other embodiments, for instance, the snare loop 914 may initially extend at an angle (e.g., a right angle) from the shaft 912. In such embodiments, the snare loop 914 may also be selectively deflectable as described herein, to allow the snare loop 914 to retrieve objects at virtually any location within a patient's vasculature or body.

Although FIGS. 9A and 9B describe an exemplary method of retrieving an object from within a pulmonary artery of a patient, it should be apparent from the disclosure herein that the surgical snares described herein may be used in numerous other manners. Indeed, the disclosed surgical snares are contemplated for use in retrieving objects from within virtually any location within a patient, and are not limited to the lungs or the pulmonary arteries. In some embodiments, for instance, a surgical snare according to the present disclosure may be used to retrieve a septal occluder or other object in a patient's heart, or may retrieve foreign or native bodies, or other objects, from a patient's kidneys, liver, or other organs, vessels, or body lumens of a patient.

The foregoing detailed description makes reference to specific exemplary embodiments. However, it will be appreciated that various modifications and changes can be made without departing from the scope contemplated herein and as set forth in the appended claims. For example, various snare devices and components may have different combinations of sizes, shapes, configurations, features, and the like. Such differences described herein are provided primarily to illustrate that there exist a number of different manners in which snare devices may be used, made, and modified within the scope of this disclosure. Different features have also been combined in some embodiments to reduce the illustrations required, and are not intended to indicate that certain features are only compatible with other features. Thus, unless a feature is expressly indicated to be used only in connection with one or more other features, such features can be used interchangeably on any embodiment disclosed herein or modified in accordance with the scope of the present disclosure. The detailed description and accompanying drawings are thus to be regarded as merely illustrative, rather than as restrictive, and all such modifications or changes, if any, are intended to fall within the scope of this disclosure.

More specifically, while illustrative exemplary embodiments in this disclosure have been more particularly described, the present disclosure is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description, which examples are to be construed as non-exclusive. Moreover, any steps recited in any method or process described herein and/or recited in the claims may be executed in any order and are not limited to the order presented in the claims, unless otherwise stated in the claims. Accordingly, the scope of the invention should be determined solely by the appended claims and their legal equivalents, rather than by the descriptions and examples given above.

What is claimed is:

1. A surgical snare, comprising:
    a steerable deflection portion, wherein said steerable deflection portion has a steerable distal tip, the steerable deflection portion is in a straight configuration in a natural state, the steerable deflection portion comprises a deflection wire disposed within said steerable distal tip, and wherein said deflection wire is configured to restrict compression of said steerable deflection portion at said distal tip and to instead cause said steerable deflection portion to bend in response to a force applied to said core wire;
    an interface linked to said steerable deflection portion, wherein said interface provides for selective manipulation of said distal tip from the natural state to a bent state;
    a snare loop disposed proximate said distal tip of said steerable deflection portion, said snare loop having a length, wherein said snare loop is configured to move as said distal tip of said steerable deflection portion is selectively deflected, and wherein said snare loop maintains said length as said distal tip is selectively deflected; and
    wherein the snare loop comprises a snare wire, at least one end of the snare wire extending proximally of the steerable deflection portion.

2. The surgical snare recited in claim 1, wherein said steerable deflection portion includes:
    a flexible elongate body between said interface and said distal tip, wherein said distal tip is configured to deflect substantially independent of said flexible elongate body in response to selective manipulation of said interface.

3. The surgical snare recited in claim 2, wherein said distal tip is a deflection tip that is configured to selectively deflect by bending relative to a longitudinal axis of said flexible elongate body to about one-hundred eighty degrees and configured to cause said snare loop to selectively undergo a corresponding amount of deflection relative to the longitudinal axis of said flexible elongate body to about one-hundred eighty degrees.

4. The surgical snare recited in claim 1, wherein said distal tip is a deflection tip that is configured to selectively deflect by bending between about zero and about ninety degrees and configured to cause said snare loop to selectively undergo a corresponding amount of deflection between about zero and about ninety degrees.

5. The surgical snare recited in claim 1, wherein said steerable deflection portion comprises a core wire linked to said interface and extending between said interface and said distal tip.

6. The surgical snare recited in claim 5, wherein said deflection wire at said distal tip of said steerable deflection portion is one end of said surgical snare loop.

7. The surgical snare recited in claim 6, wherein said distal tip is configured to selectively deflect about said deflection wire such that said deflection wire is proximate an external curve of said selectively deflected distal tip in response to an input at said interface that causes said force to be applied to said core wire.

8. The surgical snare recited in claim 1, wherein said snare loop has a shape that includes one or more of the following:
    gooseneck;
    diamond;
    hexagonal; or
    elliptical.

9. The surgical snare recited in claim 1, wherein said steerable deflection portion comprises a coiled shaft, said coiled shaft including at least a tight coil portion and a loose coil portion, said loose coil portion being positioned proximate said distal tip.

10. The surgical snare of claim 1, wherein the steerable distal tip is deflectable to sweep about an arc of more than one-hundred and eighty degrees.

11. The surgical snare of claim 1, wherein the snare loop is parallel to a longitudinal axis of the steerable distal tip in a first unstressed state.

12. The surgical snare of claim 1, wherein the at least one of the snare wire extending proximally of the steerable deflection portion extends to the proximal end of the surgical snare.

13. A surgical snare, comprising:
    a flexible body, said flexible body defining an axis;
    a distal deflecting tip attached to said flexible body, wherein said deflecting tip has at least a first, straight, natural state in a pre-deployed configuration and a second, bent state in a deployed configuration and comprises a coiled shaft and a deflection wire, wherein said deflection wire is arranged to cause said coiled shaft to flex rather than compress as said interface changes from said first position to said second position, said deflection wire having a proximal end disposed within said coiled shaft;

a core wire extending along said axis of said flexible body, wherein a distal end of said core wire is at least indirectly coupled to said deflecting tip;

an interface linked to a proximal end of said core wire, wherein said interface is selectively changeable between a first position and a second position, wherein at said first position said deflecting tip is at said first, straight, natural state in the pre-deployed configuration, and wherein at said second position said deflecting tip is at said second, bent state in the deployed configuration, said second, bent state being at least about ninety degrees offset relative to said first, straight, natural state; and a snare loop at least indirectly coupled to said deflecting tip and extending at least partially longitudinally relative to said flexible body, wherein said snare loop is configured to sweep along an arc corresponding to at least about a ninety degree rotation as said deflecting tip transitions from said first, straight, natural state in the pre-deployed configuration through said second, bent state in the deployed configuration.

14. The surgical snare recited in claim 13, wherein said core wire is directly attached to said deflecting tip.

15. The surgical snare recited in claim 13, wherein said snare loop has a length, and wherein said snare loop is configured to substantially maintain said length constant as said snare loop moves in concert with said transition of said deflecting tip from said first state through said second state.

16. The surgical snare recited in claim 13, wherein said snare loop is directly secured to one or more of said core wire, said flexible body, or said deflecting tip.

17. A surgical snare, comprising:

a flexible body, said flexible body defining an axis;

a distal deflecting tip attached to said flexible body, wherein said deflecting tip has at least a first, straight, natural state in a pre-deployed configuration and a second, bent state in a deployed configuration and comprises a coiled shaft and a deflection wire, wherein said deflection wire is arranged to cause said coiled shaft to flex rather than compress as said interface changes from said first position to said second position, said deflection wire having a proximal end disposed within said coiled shaft;

an interface linked to a proximal end of said core wire, wherein said interface is selectively changeable between a first position and a second position, wherein at said first position said deflecting tip is at said first, straight, natural state in the pre-deployed configuration, and wherein at said second position said deflecting tip is at said second, bent state in the deployed configuration, said second, bent state being at least about ninety degrees offset relative to said first, straight, natural state; and a snare loop at least indirectly coupled to said deflecting tip and extending at least partially longitudinally relative to said flexible body, wherein said snare loop is configured to sweep along an arc corresponding to at least about a ninety degree rotation as said deflecting tip transitions from said first, straight, natural state in the pre-deployed configuration through said second, bent state in the deployed configuration; and a core wire extending along said axis of said flexible body, wherein a distal end of said core wire is connected to a first end of the snare loop and the deflection wire is connected to a second end of the snare loop.

18. The surgical snare of claim 17, wherein the core wire is connected to the first end of the snare loop by laser welding or microwelding and wherein the deflection wire is connected to the second end of the snare loop by laser welding or microwelding.

* * * * *